United States Patent
Autier et al.

(10) Patent No.: US 7,727,977 B2
(45) Date of Patent: Jun. 1, 2010

(54) KYNURENINE 3-HYDROXYLASE INHIBITORS FOR THE TREATMENT OF DIABETES

(75) Inventors: Valerie Autier, Gif sur Ivette (FR);
Annick Arbellot De Vacqueur, Fontenay les Briis (FR); Gérard Moinet, Orsay (FR); Dominique Mariais, Meulan (FR); Catherine Kargar, Versailles (FR); Micheline Kergoat, Bures-sur-Yvette (FR)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 472 days.

(21) Appl. No.: 10/541,377

(22) PCT Filed: Dec. 18, 2003

(86) PCT No.: PCT/EP03/14539

§ 371 (c)(1),
(2), (4) Date: Jul. 6, 2005

(87) PCT Pub. No.: WO2004/060369

PCT Pub. Date: Jul. 22, 2004

(65) Prior Publication Data

US 2006/0142358 A1    Jun. 29, 2006

(30) Foreign Application Priority Data

Jan. 7, 2003 (FR) .................................. 03 00107
Dec. 4, 2003 (FR) .................................. 03 14263

(51) Int. Cl.
*A61K 31/33* (2006.01)
*A61K 31/194* (2006.01)
*A61K 31/235* (2006.01)
*A61K 31/426* (2006.01)
*A61P 3/10* (2006.01)

(52) U.S. Cl. .................................................. 514/183
(58) Field of Classification Search .................. 514/183
See application file for complete search history.

(56) References Cited

U.S. PATENT DOCUMENTS

| | | | |
|---|---|---|---|
| 5,877,193 A | 3/1999 | Cesura et al. | |
| 6,143,787 A * | 11/2000 | Moinet et al. | 514/568 |
| 6,288,063 B1 | 9/2001 | Ha et al. | |
| 6,323,240 B1 * | 11/2001 | Giordani et al. | 514/564 |
| 6,572,542 B1 * | 6/2003 | Houben et al. | 600/300 |
| 2003/0176476 A1 | 9/2003 | Barf et al. | |
| 2009/0076006 A1 * | 3/2009 | Qian et al. | 514/235.8 |

FOREIGN PATENT DOCUMENTS

| | | |
|---|---|---|
| EP | 0 885 869 | 12/1998 |
| WO | WO 01/90092 | 11/2001 |

OTHER PUBLICATIONS

Diabetes Research Foundation, "Diabetes and Your Eyesight," printed from http://www.glaucoma.org/learn/diabetes_and_yo.html, 2 pages.*
Naoki et al: "A Novel Enhancer of Insulinotrophic Action by High Glucose (JTT-608) Stimulates Insulin Secretion From Prancreatic Beta Cells Via a New Cellular Mechanism" Journal of Pharmacology and Experimental Therapeutics, vol. 297, No. 3, 2001, pp. 953-960.
Ohta, et al.: "JTT-608 Controls Blood Glucose by Enhancement of Glucose-Stimulated Insulin Secretion in Normal and Diabetes Mellitus Rats" European Journal of Pharmacology, vol. 367, 1999, pp. 91-99.
Shimizu, Makoto et al: "Stannous Triflate Promoted Rearrangement of beta.-keto sulfoxides. Synthesis of 1,4-Diketones" Chemistry Letters (1984) p. 1531-1534.
Kunkel, Elisabeth et al.: "Ring Opening Reactions of Methyl 2-Silyloxycyclopropanecarboxylates to 4-Oxoalkanoic Acid Derivatives" Liebigs Annalen Der Chemie (1984) p. 804.
Miyashita, Masaaki et al.: "Michael Reaction of Conjugated Nitro Olefins With Carboxylic Acid Dianion and With Ester Enolates: New Synthesis of gamma.-keto acids and gamma.-keto esters" Journal of Organic Chemistry (1984), pp. 2857-2863.
Marchand, Nathalie J. et al.: "Synthesis and Reactivity of Cross-Conjugated Polyenones With a Planar Chirality" Journal of Organic Chemistry (1996) pp. 5063-5072.
Tius, Marcus A. et al: "Synthesis of (.+-.)-xanthocidin" Tetrahedron (1996) pp. 14651-14660.
Tschesche, Rudolf et al: "Pteridines. XIV. The Synthesis of a Urothion Analog With a Methyl Side Chain" Chem. Ber (1956) pp. 89, 1054-1064.
Reissig, Hans Ulrich et al: "Selenylation, Sulfenylation, and Aminomethylation of Methyl 2-Siloxycyclopropanecarboxylates by Lewis Acid-Induced Ring Cleavage" Liebigs Annalen Der Chemie (1986) pp. 1914-1923.
Connick et al.: "The Role of Kynurenines in Diabetes Mellitus" Medical Hypotheses, vol. 18, No. 4, 1985, pp. 371-376.

* cited by examiner

*Primary Examiner*—Ardin Marschel
*Assistant Examiner*—Alicia R Hughes
(74) *Attorney, Agent, or Firm*—Millien, White, Zelano & Branigan, P.C.

(57) ABSTRACT

The present invention relates to the use of at least one compound with inhibitory activity on kynurenine 3-hydroxylase for the preparation of a medicament for the prevention and/or treatment of diabetes.

14 Claims, 6 Drawing Sheets

Figure 11:
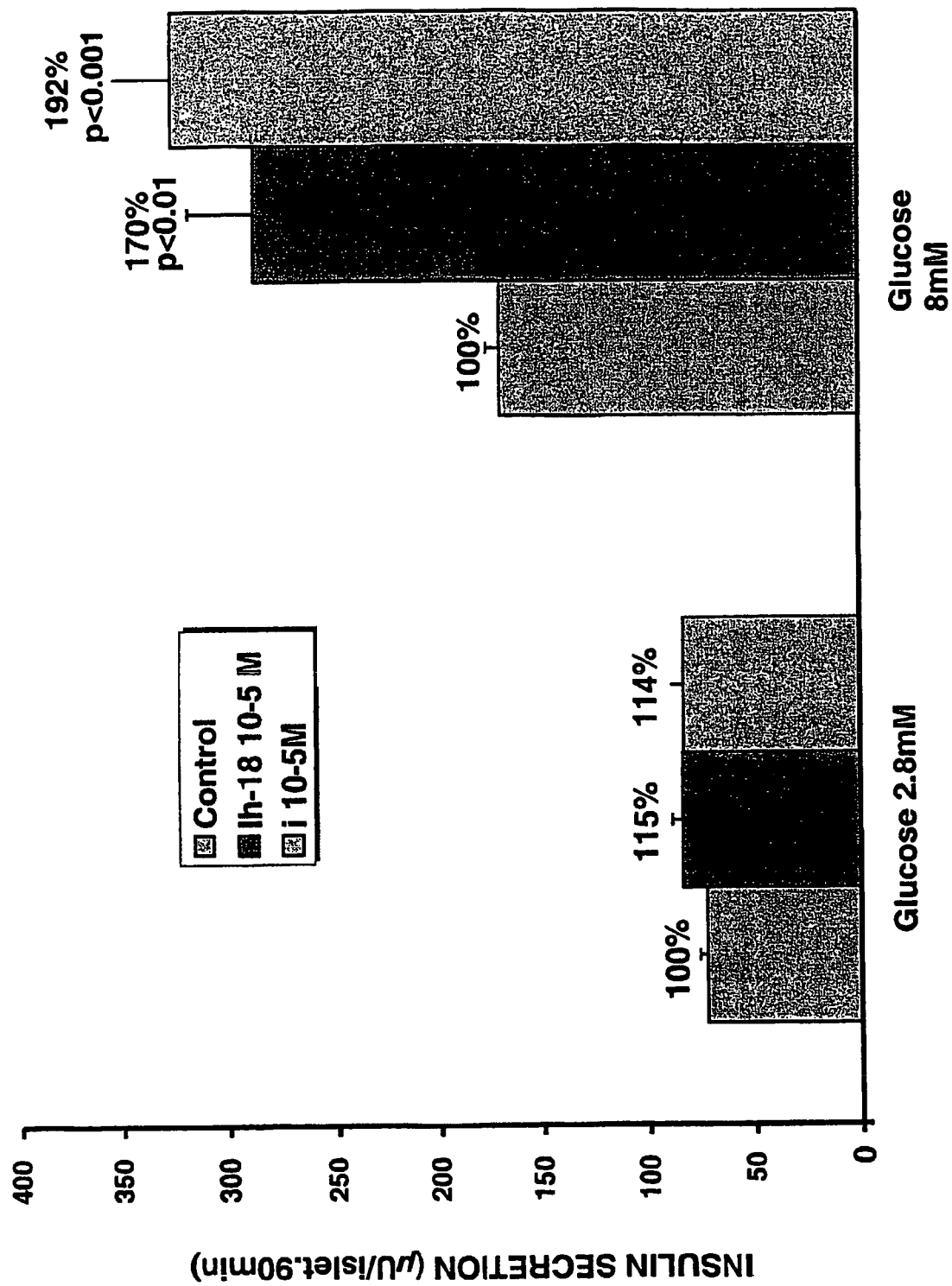

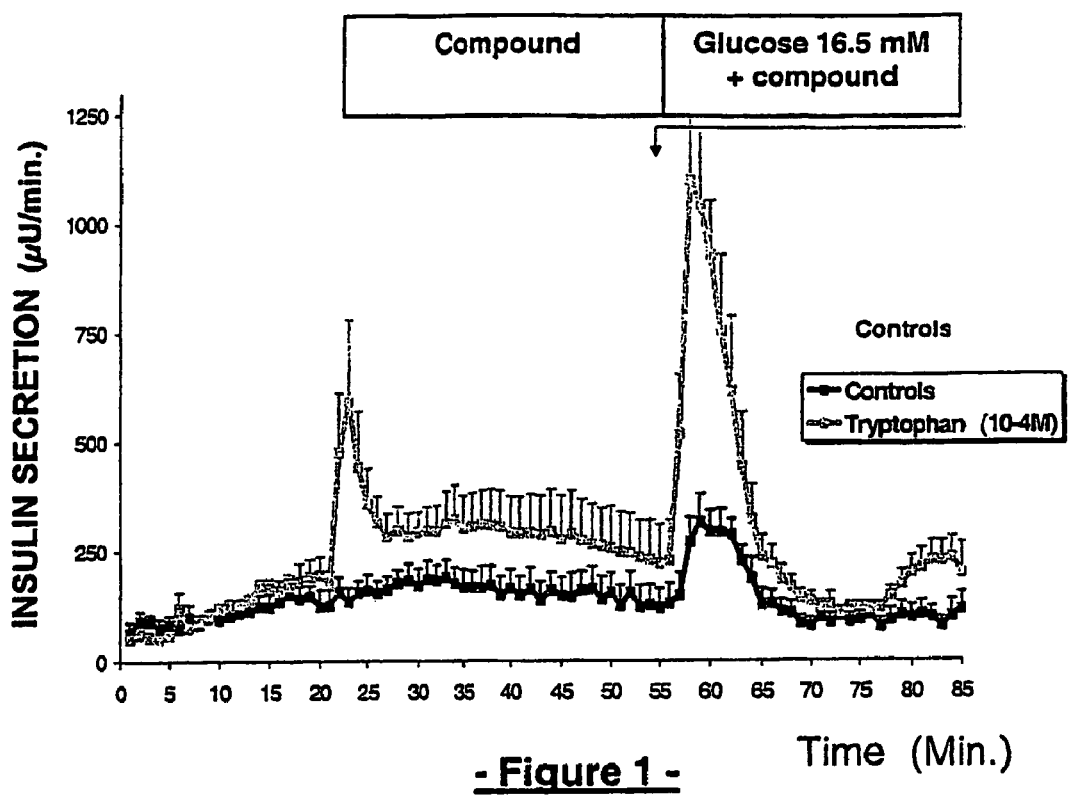
- Figure 1 -
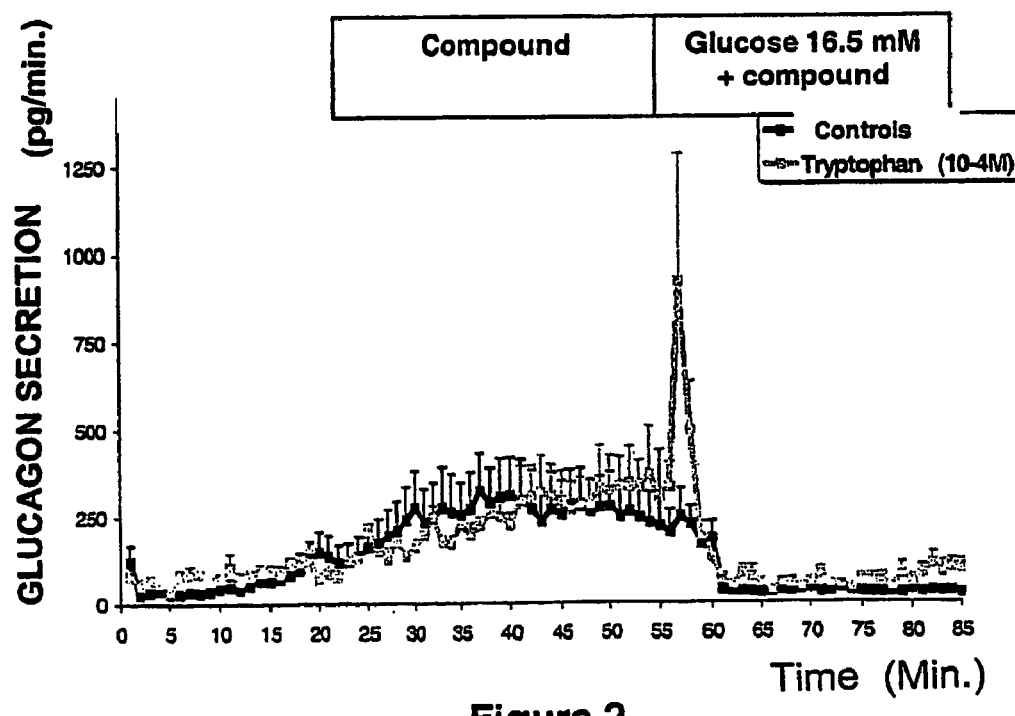
- Figure 2 -

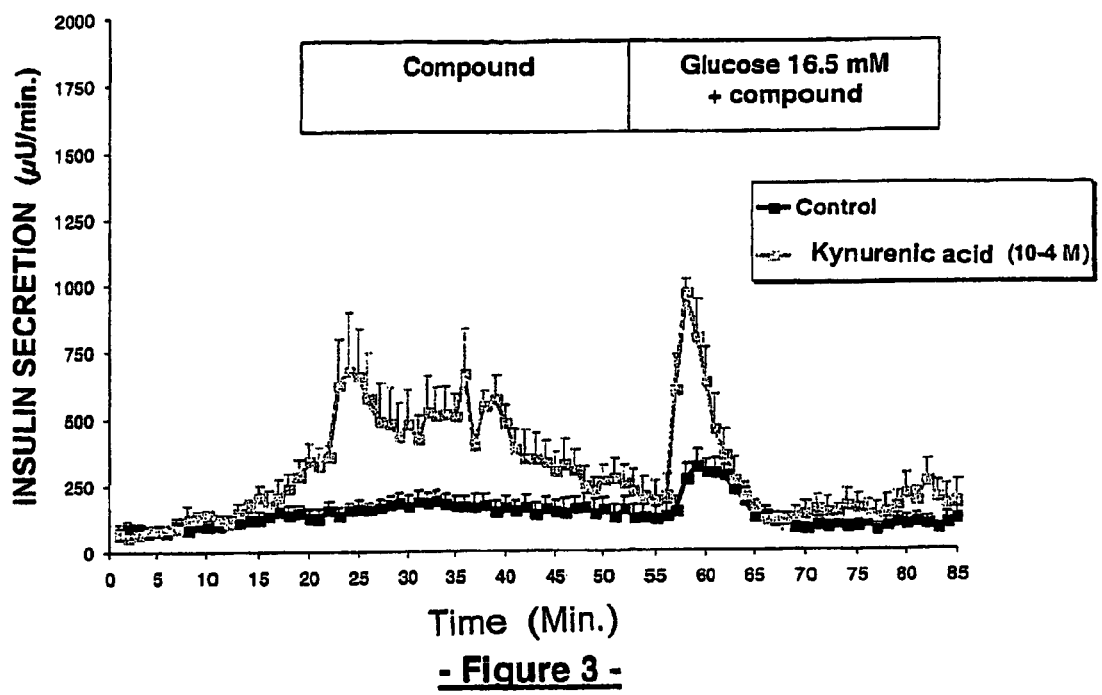
- Figure 3 -
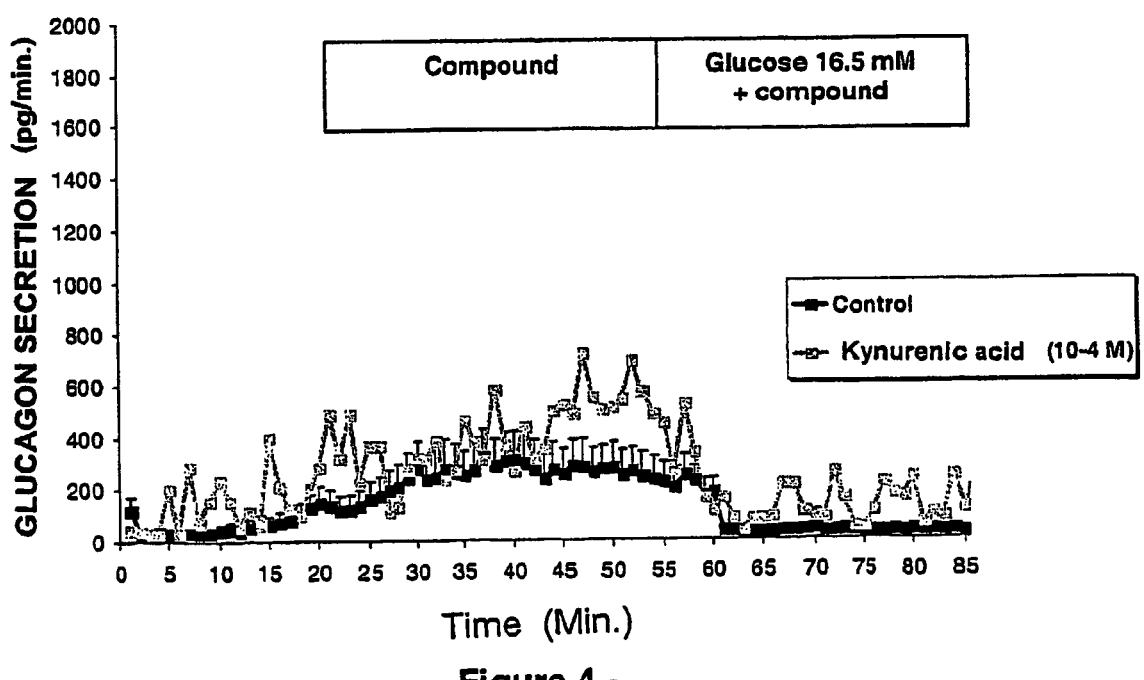
- Figure 4 -

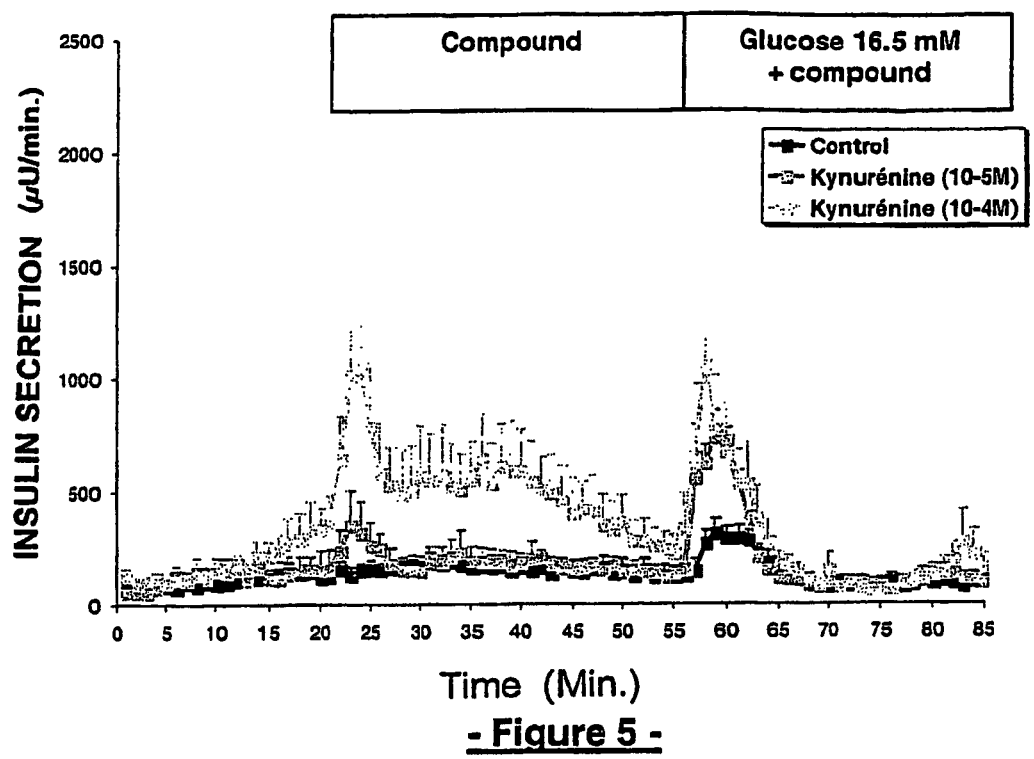
- Figure 5 -
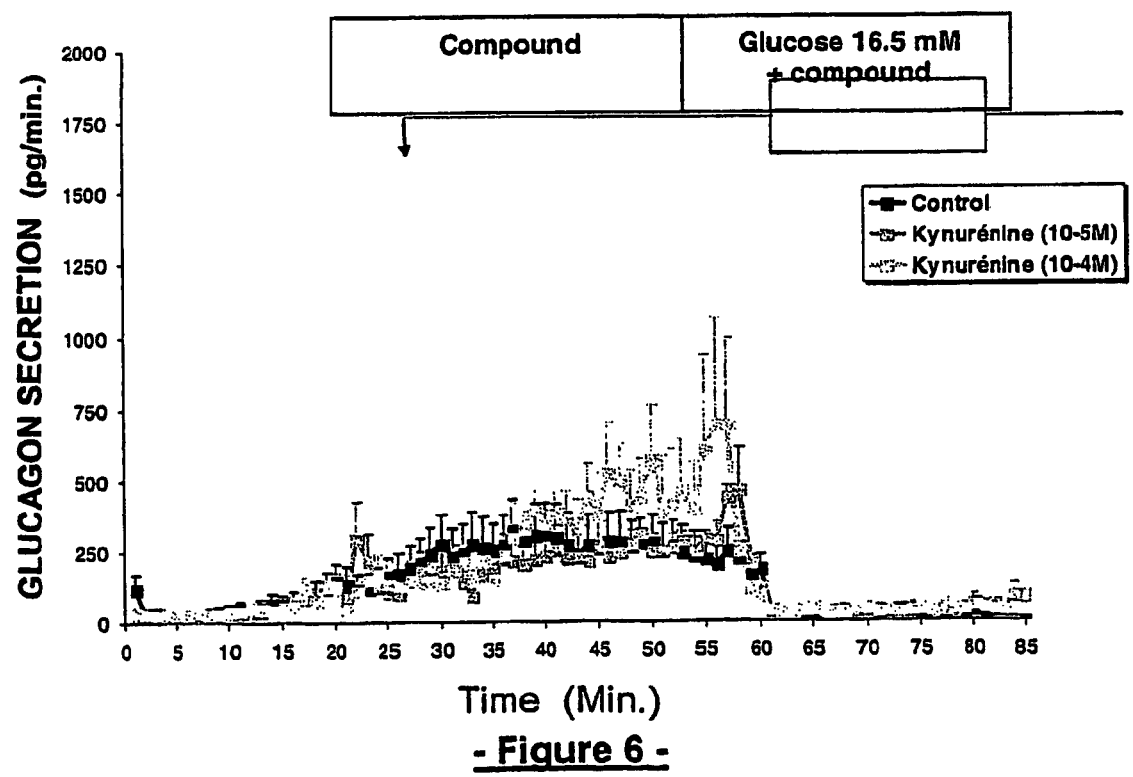
- Figure 6 -

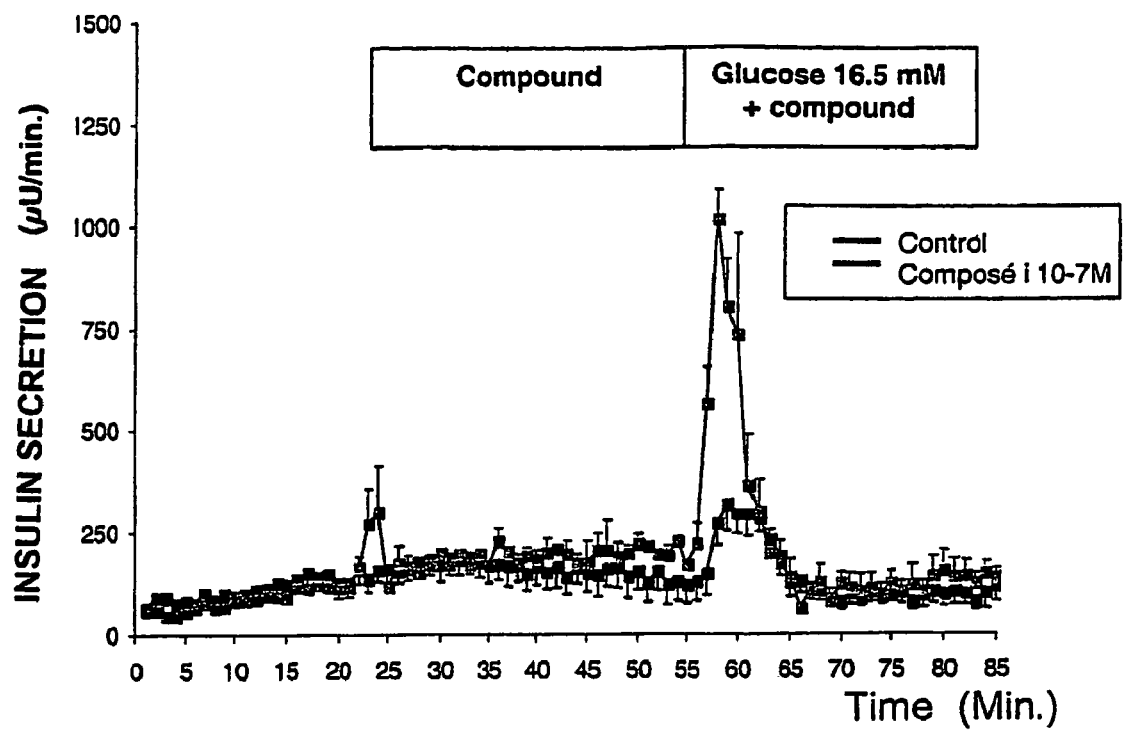
- Figure 7 -
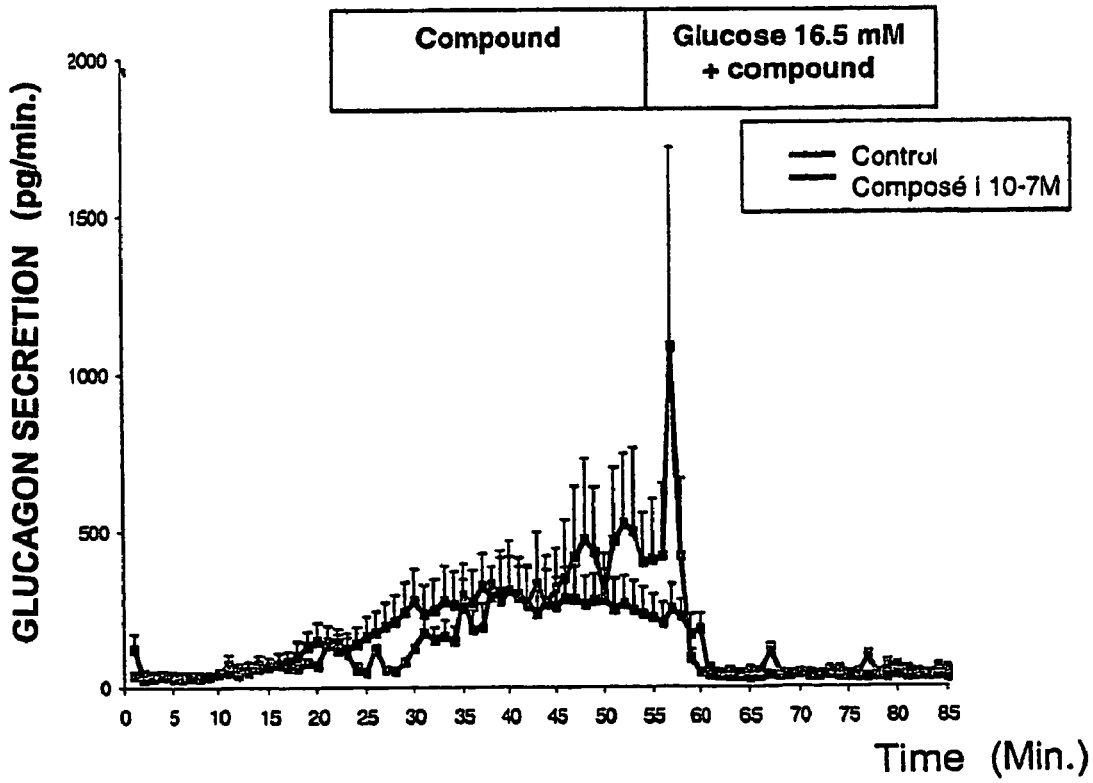
- Figure 8 -

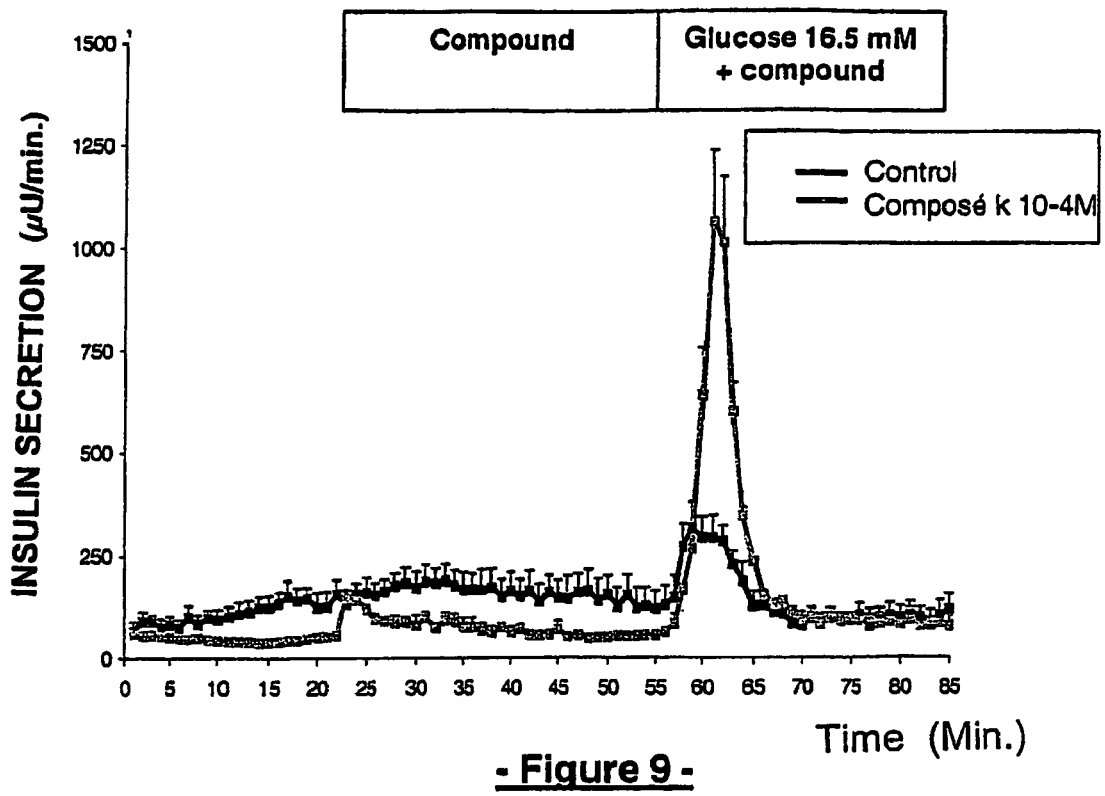
- Figure 9 -
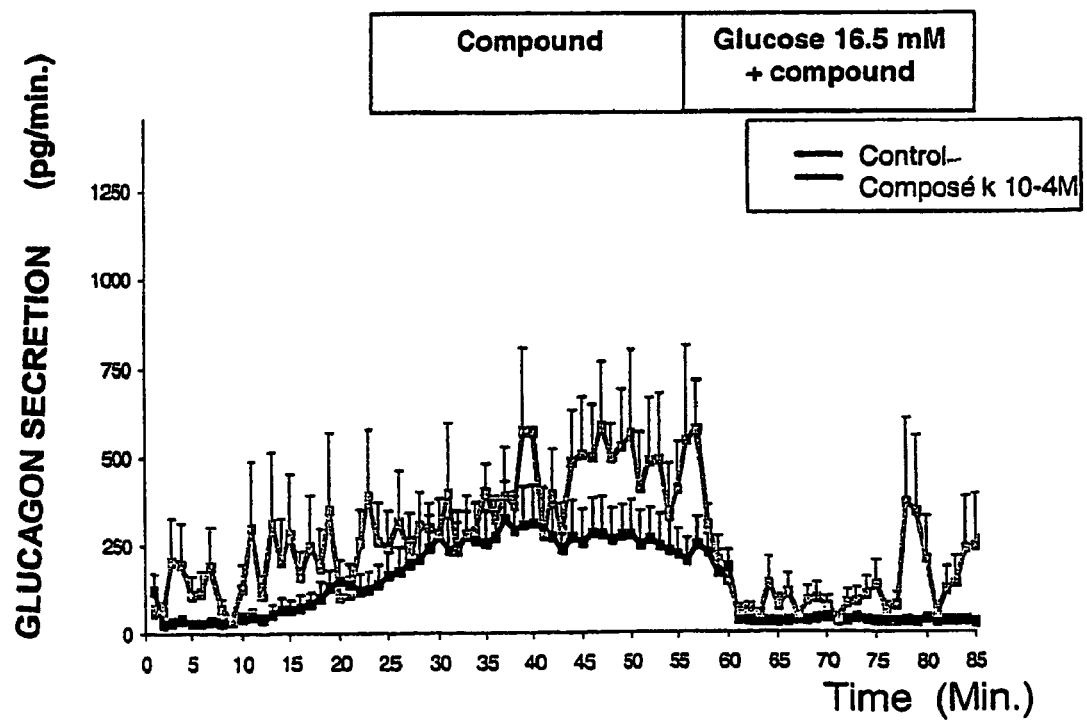
- Figure 10 -

KYNURENINE 3-HYDROXYLASE INHIBITORS FOR THE TREATMENT OF DIABETES

The present invention relates to compounds with inhibitory activity on kynurenine 3-hydroxylase and in particular to their use as pharmaceutical products for the prevention and treatment of diabetes and related pathologies.

Diabetes mellitus represents a very heterogeneous group of diseases all having a certain number of characteristics in common: elevation of glycaemia and increased long-term risk of developing cardiovascular complications.

In 1985, according to the criteria of the WHO, two major types of diabetes are distinguished: insulin-dependent diabetes (IDD), which involves the manifestation of immunological phenomena, and non-insulin-dependent is diabetes (NIDD), which were previously known as type-1 and type-2 diabetes, respectively (World Health Organization, 1985). The diabetes is said to be insulin-dependent if its symptoms (thirst, polyuria, coma, etc.) are associated with hyperglycaemia and ketosis: the administration of insulin is then vital from the early stages of the disease. In the majority of other cases, even if persistence of the hyperglycaemia secondarily necessitates the administration of insulin, the diabetes is considered as non-insulin-dependent and is treated in general using oral antidiabetic agents. Non-insulin-dependent diabetes currently affects 110 million people worldwide. This number shows no sign of decreasing, since it is forecast that 216 million people will be affected by 2010.

Maintaining a sugar balance requires strict coordination between the organs involved in energy metabolism. In particular, the liver and the pancreas are the main participants. Specifically, it has been clearly demonstrated that excessive production of glucose by the liver is responsible for fasted hyperglycaemia in diabetics (Consoli et al., *Diabetes, Vol.* 38 (1989), 550-557). Similarly, a decrease in the insulin-secretion response to glucose contributes to the development of postprandial hyperglycaemia (Polonsky et al., *N. Engl. J. Med.,* 318 (1988), 1231-39). Although many oral antidiabetic agents are currently available, none of them makes it possible to achieve normalisation of the glycaemia control parameters. The diabetic complications associated with hyperglycaemia inevitably appear. The main weak point of these-medicaments is that they address only one defect at a time, either insulin resistance (thiazolidinediones or biguanides) or insulin secretion (sulfonylureas, glinides, etc.). Furthermore, some of them have non-negligible adverse effects. Sulfonylureas in particular present a major risk of hypoglycaemia, which demands that the dosage of these medicaments be scrupulously defined and complied with from patient to patient. Simultaneous correction of the two defects mentioned above without risks of associated hypoglycaemia would constitute a fundamental breakthrough in the treatment of type II diabetes and its complications. The prevention of the associated cardiovascular risk, which represents one of the major complications, would also be of important benefit to diabetic patients.

In the present invention, the Inventors focused on a metabolic pathway, namely the metabolism of tryptophan. Tryptophan is an amino acid whose involvement in controlling carbohydrate metabolism has previously been reported (Tsiolakis D. and V. Marks, *Horm. Metabol. Res.,* 16 (1964), 226-229). Its complex metabolisation via kynurenine leads to the production of NAD+. Some of the intermediate metabolites have also been described as possibly being involved in glycaemia control (Connick J. and Stone, *Medical hypothesis,* 18 (1985), 371-376) and in particular in the mechanisms for controlling the production of glucose by the liver ("Effect of tryptophan and its metabolites on GNG in mammalian tissue", Pogson et al., 1975) and/or in insulin secretion and synthesis (Noto Y. and Okamoto, *Acta Diabet. Lat,* 15 (1978), 273-282; Rogers and Evangelista, *Proc. Soc. Exp.,* 178 (1985), 275-278). Among the active metabolites of this pathway are tryptophan itself, kynurenine and kynurenic acid. The concentration of these metabolites is controlled by three enzymes: kynurenine 3-hydroxylase, kynureninase and kynurenine aminotransferase. Kynurenine aminotransferase has also been suspected of being involved in the hypertension physiopathology of SHR rats (Spontaneously Hypertensive Rat; Kwok et al., JBC, 35779-35782, September 2002) which are otherwise insulin-resistant. Despite that, the joint action of these metabolites on glucose production by the liver and on insulin secretion in response to glucose has not been demonstrated in the prior art. In particular, it has not been demonstrated that some of these metabolites can restore a physiological response to glucose, the secretion of the pancreatic hormones (insulin and glucagon), in animals rendered diabetic by injection of streptozotocin, which would thus make it possible to correct the insulin secretion defect without giving rise to any risk of hypoglycaemia.

It is well described in the prior art that certain metabolites of the kynurenine pathway, such as quinolinic acid and kynurenic acid, act as neuro-toxic-agents and neuroprotective agents, respectively, on the nervous system. These effects are linked to their capacity to modulate glutamate receptors and/or nicotinic receptors (Schwarcz R. and Pellicciardi R., *JPET* 303 (2002), 1-10; Stone and Darlington, *Nature Reviews,* 1(2002), 609-620). The presence of glutamate receptors in the pancreas is described in the prior art, as is their involvement in pancreatic hormone secretion (Weaver C. et al., *J. Biol. Chem.,* 271 (1996), 12977-12984), but it has not been demonstrated that these glutamate receptors are controlled by the kynurenine metabolites in this organ.

The research conducted with the aim of meeting the objectives of the present invention has made it possible to demonstrate, surprisingly, that the modulation of tryptophan metabolism in the kynurenine pathway via the hepatic, pancreatic and cardiac inhibition of kynurenine 3-hydroxylase plays an important role in the prevention and treatment of diabetic diseases, in particular non-insulin-dependent diabetes and its complications.

One of the objectives of the present invention consequently consists in providing novel therapeutic means which have curative and/or preventive activity on diabetes and associated pathologies and which are free of the risk of hypoglycaemia.

The present invention also proposes, as another objective, a process for the treatment of diabetes that makes it possible to avoid the side effects and especially hypoglycaemia, the said process using therapeutic means whose mechanism of action for this type of pathology is not described or suggested in the prior art.

Specifically, certain compounds are known (see U.S. Pat. No. 6,048,896 and U.S. Pat. No. 6,323,240), which have inhibitory activity on the kynurenine 3-hydroxylase and which are useful in the treatment of neurodegenerative diseases, including diseases of the central nervous system, sclerosis and glaucomarelated retinopathy. Such compounds were already known as having analgesic and anti-inflammatory properties.

The research conducted with the aim of meeting the objectives of the present invention has made it possible to demonstrate, surprisingly, that the inhibition of kynurenine 3-hydroxylase plays an important role in the prevention and treatment of diabetic diseases, in particular non-insulin-dependent diabetes and its complications.

It has thus been discovered that compounds with inhibitory activity on kynurenine 3-hydroxylase are active in the prevention and treatment of diabetes and related pathologies.

One of the subjects of the present invention is, consequently, the use of at least one compound with inhibitory activity on kynurenine 3-hydroxylase, for the preparation of a medicament for the prevention and/or treatment of diabetes, especially non-insulin-dependent diabetes, and its complications.

It has especially been discovered that the compounds corresponding to the general formula (I) or to the general formula (II) described hereinbelow generally have an inhibitory activity on kynurenine 3-hydroxylase. Among the compounds described in formulae (I) and (II), some families of compounds are known to have activity that is useful in the treatment of diabetes, and especially the families of compounds corresponding to patent application WO-A-98/07681 and the families corresponding to patent application EP-A-0 885 869. The compounds with substantial activity on kynurenine 3-hydroxylase are especially preferred. The term "substantial activity" means any inhibitory activity on the enzyme by the in vitro test process defined below, thus making it possible to obtain an effective therapeutic action on the enzyme. In particular, an enzymatic activity of less than or equal to 70%, advantageously less than or equal to 50% and even more preferably less than or equal to 30% relative to the control, is preferred.

It has thus been discovered that, within these families of compounds, it is possible to use compounds that are characterised by inhibitory activity on kynurenine 3-hydroxylase to obtain an improved treatment or improved medicaments, or for a different purpose, to prevent or treat diabetes, and especially non-insulin-dependent diabetes, and also the complications of this diabetes, via a novel route that offers unexpected advantages. They also make it possible to improve the prevention and treatment of diabetes, especially of non-insulin-dependent diabetes, by administration of a therapeutically effective amount to patients in need of inhibition of kynurenine 3-hydroxylase.

In particular, the compounds of family Ih are found to be noteworthy kynurenine 3-hydroxylase inhibitors and antidiabetic agents. Confirmation of the existence of inhibitory activity on kynurenine 3-hydroxylase may be made by any known means and especially, in a particularly simple manner, by subjecting the compound to an in vitro test that will be defined hereinbelow.

More specifically, the compounds with inhibitory activity on kynurenine 3-hydroxylase belong to the general formula (I) or to the general formula (II) below:

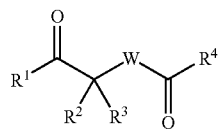

(I)

-continued

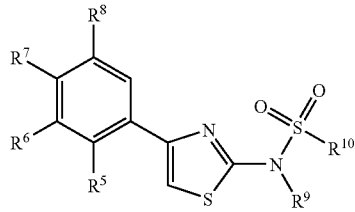

(II)

in which:
W represents a divalent radical chosen from the following radicals:

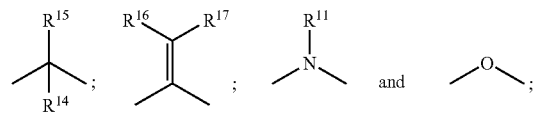

$R^1$ represents a radical chosen from linear or branched alkyl containing from 1 to 14 carbon atoms and optionally substituted, alkenyl, alkynyl, cycloalkyl, cycloalkenyl, a heterocyclic radical, an aryl radical and a heteroaryl radical;

$R^2$ is chosen from hydrogen, a halogen atom, hydroxyl, thiol, carboxyl, alkyl, alkenyl, alkynyl, alkoxy, alkylthio, alkylcarbonyl, alkoxycarbonyl, aryl, heteroaryl, cycloalkyl and a heterocyclic radical;

$R^3$ is chosen from hydrogen, a halogen atom, hydroxyl, thiol, alkyl, alkenyl, alkynyl, alkoxy, alkylthio, aryl, heteroaryl, cycloalkyl and a heterocyclic radical;

$R^2$ and $R^3$ together also possibly forming a group $=CR^{16}R^{17}$; or alternatively together forming, with the carbon atom that bears them, a cycloalkyl radical or a heterocyclic radical;

$R^4$ is chosen from hydroxyl, alkoxy, alkenyloxy, alkynyloxy, aryloxy, heteroaryloxy, —N($R^{12}R^{12'}$), —N($R^{12}$)$OR^{13}$, linear or branched alkyl containing from 1 to 14 carbon atoms and optionally substituted, alkenyl, alkynyl, cycloalkyl, cycloalkenyl, aryl, heteroaryl and a heterocyclic radical;

$R^5$, $R^6$, $R^7$ and $R^8$, which may be identical or different, are chosen, independently of each other, from hydrogen, a halogen atom, and a nitro, cyano, hydroxyl, trifluoromethyl, alkyl, alkoxy, cycloalkyl or aryl radical; the radicals $R^5$ and $R^6$, on the one hand, or $R^8$ and $R^7$, on the other hand, may also form, together with the carbon atoms to which they are attached, a benzene ring optionally substituted by one or more groups, which may be identical or different, chosen from a halogen atom, a trifluoromethyl, cyano or nitro radical, an alkyl radical and an alkoxy radical;

$R^9$ represents hydrogen or an alkyl radical;

$R^{10}$ is chosen from an alkyl, an aryl and a heteroaryl radical;

$R^{12}$ and $R^{12'}$, which may be identical or different, are chosen, independently of each other, from hydrogen and an alkyl, alkenyl, alkynyl, alkylcarbonyl, aryl or heteroaryl radical; or alternatively $R^{12}$ and $R^{12'}$ may form, together with the nitrogen atom to which they are attached, a monocyclic or bicyclic heterocyclic group containing a total of 5 to 10 atoms, among which 1, 2, 3 or 4 are chosen, independently of each other, from nitrogen, oxygen and sulfur, the said heterocyclic radical also optionally comprising 1, 2, 3 or 4 double bonds and optionally being substituted by one or more chemical groups, which may be identical or different, chosen from hydroxyl, halogen atom, alkyl, alkenyl, alkynyl, alkoxy, alkylthio, aryl, heteroaryl, heterocyclic radical and trifluoromethyl;

$R^{13}$ is chosen from hydrogen and an alkyl, alkenyl, alkynyl, aryl, heteroaryl, —N($R^{12}R^{12'}$) or —N($R^{12}$)O$R^{13}$ radical;

$R^{14}$ is chosen from hydrogen, a halogen atom, hydroxyl, thiol, carboxyl, alkyl, alkenyl, alkynyl, alkoxy, alkylthio, alkylcarbonyl, alkoxycarbonyl, aryl, arylalkyl, heteroaryl, cycloalkyl and a heterocyclic radical;

$R^{14}$ may also form a bond with $R^2$, thus forming a double bond between the carbon atoms respectively bearing the substituents $R^{14}$ and $R^2$; or alternatively $R^{14}$ forms, with $R^2$ and with the carbon atoms that bear them, a ring containing a total of 3, 4, 5, 6 or 7 carbon atoms, among which 1, 2 or 3 may be replaced with an atom chosen from nitrogen, oxygen and sulfur, the said ring possibly comprising one or more unsaturations in the form of (a) double bond(s), and being optionally substituted by one or more radicals, which may be identical or different, chosen from oxo, alkoxy, alkoxycarbonyl and alkylcarbonyloxy;

$^{15}$ is chosen from hydrogen, a halogen atom, hydroxyl, thiol, carboxyl, alkyl, alkenyl, alkynyl, alkylcarbonyl, alkoxycarbonyl, alkoxy, alkenyloxy, alkynyloxy, aryloxy, cycloalkyloxy, heteroaryloxy, heterocyclyloxy, alkylthio, alkenylthio, alkynylthio, arylthio, cycloalkylthio, heteroarylthio, heterocyclylthio, aryl, heteroaryl, cycloalkyl and a heterocyclic radical;

$R^{14}$ and $R^{15}$ also possibly forming, together with the carbon atom that bears them, a cycloalkyl radical or a heterocyclic radical;

$R^{16}$ and $R^{17}$, which may be identical or different, are chosen, independently of each other, from hydrogen, a halogen atom, an alkyl, aryl, heteroaryl or cycloalkyl radical and a heterocyclic radical; or alternatively $R^{16}$ and $R^{17}$ form, together with the carbon atom that bears them, a cycloalkyl radical or a heterocyclic radical; and $R^{11}$ is chosen from hydrogen and an alkyl, aryl, arylalkyl, heteroaryl, heteroarylalkyl, cycloalkyl or cycloalkylalkyl radical, and any protecting group for an amine function;

and also the possible geometrical and/or optical isomers thereof, and possible tautomeric forms thereof;

the solvates and hydrates of these compounds;

and also the possible salts thereof with a pharmaceutically acceptable acid or base, or alternatively the pharmaceutically acceptable prodrugs of these compounds.

The following definitions specify the natures of the various groups and radicals defined above. Unless otherwise indicated, these definitions apply for all the terms of the present invention thus explained.

The term "halogen atom" denotes a fluorine, chlorine, bromine or iodine atom.

The term "alkyl" denotes a linear or branched alkyl radical containing from 1 to 6 carbon atoms, optionally substituted by one or more chemical groups chosen from hydroxyl, carboxyl, cyano, nitro, —N($R^{12}R^{12'}$), —N($R^{12}$)O$R^{13}$, aryl, heteroaryl, cycloalkyl, heterocyclic radical, alkyl, alkenyl, alkynyl, alkoxy, alkylcarbonyl, alkoxycarbonyl, halogen atom, trifluoromethyl, thiol, —S$R^{13'}$, —S(O)$R^{13'}$ and —S(O$_2$)$R^{13'}$, with $R^{13'}$ having the same definition as $R^{13}$, with the exception of hydrogen. The possible substituents on the alkyl radical containing from 1 to 14 carbon atoms may be identical to those described above.

The term "alkenyl" denotes an alkenyl radical containing one or more double bonds; the said radical, which is linear or branched, and which contains from 2 to 6 carbon atoms, is optionally substituted by one or more chemical groups chosen from hydroxyl, carboxyl, cyano, nitro, —N($R^{12}R^{12'}$), —N($R^{12}$)O$R^{13}$, aryl, heteroaryl, cycloalkyl, heterocyclic radical, alkyl, alkenyl, alkynyl, alkoxy, alkylcarbonyl, alkoxycarbonyl, halogen atom, trifluoromethyl, thiol, —S$R^{13'}$, —S(O)$R^{13'}$ and —S(O$_2$)$R^{13'}$, with $R^{13'}$ having the same definition as $R^{13}$, with the exception of hydrogen.

The term "alkynyl" denotes an alkynyl radical containing one or more triple bonds; the said radical, which is linear or branched, and which contains from 2 to 6 carbon atoms, is optionally substituted by one or more chemical groups chosen from hydroxyl, carboxyl, cyano, nitro, —N($R^{12}R^{12'}$), —N($R^{12}$)O$R^{13}$, aryl, heteroaryl, cycloalkyl, heterocyclic radical, alkyl, alkenyl, alkynyl, alkoxy, alkylcarbonyl, alkoxycarbonyl, halogen atom, trifluoromethyl, thiol, —S$R^{13'}$, —S(O)$R^{13'}$ and —S(O$_2$)$R^{13'}$, with $R^{13'}$ having the same definition as $R^{13}$, with the exception of hydrogen.

The term "alkoxy" should be understood as being "alkyl"+"oxy", in which the term "alkyl" is as defined above. The substituents of the alkoxy radical are identical to those defined for the alkyl radical.

The term "cycloalkyl" denotes a bridged or non-bridged monocyclic, bicyclic or tricyclic cycloalkyl radical containing from 3 to 13 carbon atoms, optionally substituted by one or more chemical groups, which may be identical or different, chosen from hydroxyl, carboxyl, cyano, nitro, —N($R^{12}R^{12'}$), —N($R^{12}$)O$R^{13}$, aryl, heteroaryl, cycloalkyl, heterocyclic radical, alkyl, alkenyl, alkynyl, alkoxy, alkylcarbonyl, alkoxycarbonyl, halogen atom, trifluoromethyl, thiol, —S$R^{13'}$, —S(O)$R^{13'}$ and —S(O$_2$)$R^{13'}$, with $R^{13'}$ having the same definition as $R^{13}$, with the exception of hydrogen.

The term "cycloalkenyl" denotes a cycloalkyl radical as defined above comprising at least one double bond.

The term "heterocyclic radical" or "heterocyclyl" denotes a monocyclic or bicyclic radical containing a total of 5 to 10 atoms, among which 1, 2, 3 or 4 are chosen, independently of each other, from nitrogen, oxygen and sulfur, the said heterocyclic radical also optionally comprising 1, 2, 3 or 4 double bonds and being optionally substituted by one or more chemical groups, which may be identical or different, chosen from hydroxyl, carboxyl, cyano, nitro, —N($R^{12}R^{12'}$), —N($R^{12}$)O$R^{13}$, aryl, heteroaryl, cycloalkyl, heterocyclic radical, alkyl, alkenyl, alkynyl, alkoxy, alkylcarbonyl, alkoxycarbonyl, halogen atom, trifluoromethyl, thiol, —S$R^{13'}$, —S(O)$R^{13'}$ and —S(O$_2$)$R^{13'}$, with $R^{13'}$ having the same definition as $R^{13}$, with the exception of hydrogen.

The term "aryl" denotes a monocyclic, bicyclic or tricyclic aryl radical containing from 6 to 14 carbon atoms, optionally substituted by one or more chemical groups, which may be identical or different, chosen from hydroxyl, carboxyl, cyano, nitro, —N($R^{12}R^{12'}$), —N($R^{12}$)O$R^{13}$, aryl, heteroaryl, cycloalkyl, heterocyclic radical, alkyl, alkenyl, alkynyl, alkoxy, alkylcarbonyl, alkoxycarbonyl, halogen atom, trifluoromethyl, thiol, —S$R^{13'}$, —S(O)$R^{13'}$ and —S(O$_2$)$R^{13'}$, with $R^{13'}$ having the same definition as $R^{13}$, with the exception of hydrogen.

The term "heteroaryl" denotes a monocyclic or bicyclic heteroaryl radical containing a total of 5 to 10 atoms, among which 1, 2, 3 or 4 are chosen, independently of each other, from nitrogen, oxygen and sulfur, the said heteroaryl radical being optionally substituted by one or more chemical groups, which may be identical or different, chosen from hydroxyl, carboxyl, cyano, nitro, —N($R^{12}R^{12'}$), —N($R^{12}$)O$R^{13}$, aryl, heteroaryl, cycloalkyl, heterocyclic radical, alkyl, alkenyl, alkynyl, alkoxy, alkylcarbonyl, alkoxycarbonyl, halogen atom, trifluoromethyl, thiol, —S$R^{13'}$, —S(O)$R^{13'}$ and —S(O$_2$)$R^{13'}$, with $R^{13'}$ having the same definition as $R^{13}$, with the exception of hydrogen.

A preferred aryl radical is the phenyl radical or the 1-naphthyl, 2-naphthyl or fluorenyl radical.

Among the alkyl and alkoxy radicals substituted by an aryl radical, the benzyl, benzyloxy, phenethyl, phenylethoxy, naphthylmethyl and naphthylmethoxy radicals are particularly preferred.

Among the cycloalkyl radicals that are preferred are cyclopropyl, cyclopentyl, cyclohexyl, the adamantyl radical and radicals derived from tetralin and from decalin.

The terms "heteroaryl radical" and "heterocyclic radical" preferably mean a pyridyl, furyl, thienyl, 1-quinolyl, 2-quinolyl, tetrahydrofuryl, tetrahydropyranyl, pyrrolyl, imidazolyl, pyrazolyl, thiazolyl, isothiazolyl, oxazolyl, isoxazolyl, morpholino, piperazinyl, piperidyl, pyranyl, thiopyranyl, indanyl, benzothienyl or benzofuryl radical.

For the compounds of the formulae (I) and (II) presented above, the term "geometrical isomer" means a cis/trans or E/Z isomerism. More particularly, for the compounds of the formula (I) and when $R^{14}$ forms a bond with $R^2$, thus forming a double bond between the carbon atoms respectively bearing the substituents $R^{14}$ and $R^2$, this double bond may be of E or Z configuration. These geometrical isomers, which may or may not be pure, alone or as a mixture, form an integral part of the compounds of the formula (I).

The term "optical isomer" includes all the forms of isomers, alone or as mixtures, arising from the presence of one or more axes and/or centres of symmetry in the molecule, and resulting in the rotation of a beam of polarised light. The term "optical isomer" more particularly includes the enantiomers and diastereoisomers, in pure form or as a mixture.

In particular, for the compounds of the formula (I), and when the substituents $R^2$ and $R^3$, on the one hand, and/or the substituents $R^{16}$ and $R^{17}$, on the other hand, are different, the carbon atoms bearing these pairs of substituents are asymmetric, and thus lead to enantiomers and/or diastereoisomers. These optical isomers, which may or may not be pure, alone or as a mixture, form an integral part of the compounds of the formula (I).

Among the acids capable of forming pharmaceutically acceptable salts with the compounds of the formula (I) or of the formula (II) above, non-limiting examples that may be mentioned include hydrochloric acid, phosphoric acid, sulfuric acid, tartaric acid, citric acid, maleic acid, acetic acid, fumaric acid, alkylsulfonic acid and camphoric acid.

Among the bases capable of forming pharmaceutically acceptable salts with the compounds of the formula (I) or of the formula (II) above, non-limiting examples that may be mentioned include sodium hydroxide, potassium hydroxide, diethylamine, triethylamine, ethanolamine, diethanolamine, arginine and lysine.

The compounds of the formulae (I) and (II) above also comprise the prodrugs of these compounds.

The term "prodrugs" means compounds which, once administered to the patient, are chemically and/or biologically transformed by the living body, into compounds of the formula (I) or (II).

Examples of prodrugs of compounds of the formula (I) above are those for which $R^4$ represents a radical —OP, in which P is a leaving group, for example a sugar residue, such as sucrose, which can thus lead to compounds in which $R^4$ represents —OH. Such prodrugs are included in the field of the present invention.

A large number of compounds of the formulae (I) and (II) defined above are known, especially by the patent publications and patent applications U.S. Pat. No. 6,048,896, U.S. Pat. No. 6,323,240, EP 0 885 869 and U.S. Pat. No. 5,877, 193. These publications provide the processes for the preparation of these various compounds, to which processes a person skilled in the art may refer, or may adapt, to synthesise all the compounds of the formulae (I) and (II).

According to one variant of the present invention, the compounds of the formula (I) that are preferred are those having the following characteristics, taken separately or in combination:

W represents a divalent radical chosen from the following radicals:

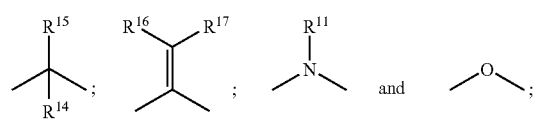

$R^1$ represents a radical chosen from linear or branched alkyl containing from 1 to 14 carbon atoms and optionally substituted, alkenyl, cycloalkyl, cycloalkenyl, a heterocyclic radical, an aryl radical and a heteroaryl radical;

$R^2$ is chosen from hydrogen, a halogen atom, hydroxyl, thiol, carboxyl, alkyl, alkenyl, alkoxy, alkylthio, alkylcarbonyl, alkoxycarbonyl and aryl;

$R^3$ is chosen from hydrogen, a halogen atom, hydroxyl, thiol, alkyl, alkenyl, alkoxy, alkylthio and aryl;

$R^2$ and $R^3$ together also possibly forming a group =C$R^{16}R^{17}$;

$R^4$ is chosen from hydroxyl, alkoxy, alkenyloxy, alkynyloxy, aryloxy, heteroaryloxy, —N($R^{12}R^{12'}$), —N($R^{12}$)O$R^{13}$, linear or branched alkyl containing from 1 to 14 carbon atoms and optionally substituted, cycloalkyl, cycloalkenyl, aryl, heteroaryl and a heterocyclic radical;

$R^{12}$ and $R^{12'}$, which may be identical or different, are chosen, independently of each other, from hydrogen and an alkyl, alkenyl, alkynyl, alkylcarbonyl, aryl or heteroaryl radical;

$R^{13}$ is chosen from hydrogen and an alkyl, alkenyl, alkynyl, aryl, —N($R^{12}R^{12'}$) or —N($R^{12}$)O$R^{13}$ radical;

$R^{14}$ is chosen from hydrogen, a halogen atom, hydroxyl, thiol, carboxyl, alkyl, alkenyl, alkoxy, alkylthio, alkylcarbonyl, alkoxycarbonyl, aryl and arylalkyl;

$R^{14}$ may also form a bond with $R^2$, thus forming a double bond between the carbon atoms respectively bearing the substituents $R^{14}$ and $R^2$; or alternatively $R^{14}$ forms, with $R^2$ and with the carbon atoms that bear them, a ring containing a total of 3, 4, 5 or 6 carbon atoms, among which 1, 2 or 3 may be replaced with an atom chosen from nitrogen and oxygen, the said ring possibly comprising one or more unsaturations in the form of (a) double bond(s), and being optionally substituted by one or more radicals, which may be identical or different, chosen from oxo, alkoxy, alkoxycarbonyl and alkylcarbonyloxy;

$R^{15}$ is chosen from hydrogen, a halogen atom, hydroxyl, thiol, carboxyl, alkyl, alkenyl, alkylcarbonyl, alkoxycarbonyl, alkoxy, alkylthio and aryl;

$R^{16}$ is chosen from hydrogen and an alkyl or aryl radical;

$R^{17}$ represents a hydrogen atom; and $R^{11}$ is chosen from hydrogen and any protecting group for an amine function;

and also the possible geometrical and/or optical isomers thereof, and possible tautomeric forms thereof;

the solvates and hydrates of these compounds;

and the possible salts thereof with a pharmaceutically acceptable acid or base, or alternatively the pharmaceutically acceptable prodrugs of these compounds.

According to another variant of the present invention, this invention relates to the use of compounds of the formula (Ia) that have inhibitory activity on kynurenine 3-hydroxylase, for the preparation of a medicament for the prevention and/or treatment of diabetes. These compounds of the formula (Ia) have the general structure (I) as defined above, in which:

W represents a divalent radical chosen from the following radicals:

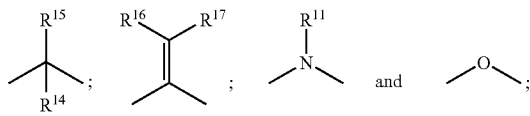

$R^1$ represents a radical chosen from linear or branched alkyl containing from 1 to 14 carbon atoms and optionally substituted, alkenyl, alkynyl, cycloalkyl, cycloalkenyl, a heterocyclic radical, an aryl radical and a heteroaryl radical;

$R^2$ is chosen from hydrogen, a halogen atom, hydroxyl, thiol, carboxyl, alkyl, alkenyl, alkynyl, alkoxy, alkylthio, alkylcarbonyl, alkoxycarbonyl, aryl, heteroaryl, cycloalkyl and a heterocyclic radical;

$R^3$ is chosen from hydrogen, a halogen atom, hydroxyl, thiol, alkyl, alkenyl, alkynyl, alkoxy, alkylthio, aryl, heteroaryl, cycloalkyl and a heterocyclic radical;

$R^2$ and $R^3$ together also possibly forming a group $=CR^{16}R^{17}$, or alternatively forming, together with the carbon atom that bears them, a cycloalkyl radical or a heterocyclic radical;

$R^4$ is chosen from hydroxyl, alkoxy, alkenyloxy, alkynyloxy, aryloxy, heteroaryloxy, —$N(R^{12}R^{12'})$, —$N(R^{12})OR^{13}$, linear or branched alkyl containing from 1 to 14 carbon atoms and optionally substituted, alkenyl, alkynyl, cycloalkyl, cycloalkenyl, aryl, heteroaryl and a heterocyclic radical;

$R^{12}$ and $R^{12'}$, which may be identical or different, are chosen, independently of each other, from hydrogen and an alkyl, alkenyl, alkynyl, alkylcarbonyl, aryl or heteroaryl radical; or alternatively $R^{12}$ and $R^{12'}$ may form, together with the nitrogen atom to which they are attached, a monocyclic or bicyclic heterocyclic group containing a total of 5 to 10 atoms, among which 1, 2, 3 or 4 are chosen, independently of each other, from nitrogen, oxygen and sulfur, the said heterocyclic radical also optionally comprising 1, 2, 3 or 4 double bonds and optionally being substituted by one or more chemical groups, which may be identical or different, chosen from hydroxyl, halogen atom, alkyl, alkenyl, alkynyl, alkoxy, alkylthio, aryl, heteroaryl, heterocyclic radical and trifluoromethyl;

$R^{13}$ is chosen from hydrogen and an alkyl, alkenyl, alkynyl, aryl, heteroaryl, —$N(R^{12}R^{12'})$ or —$N(R^{12})OR^{13}$ radical;

$R^{14}$ is chosen from hydrogen, a halogen atom, hydroxyl, thiol, carboxyl, alkyl, alkenyl, alkynyl, alkoxy, alkylthio, alkylcarbonyl, alkoxycarbonyl, aryl, arylalkyl, heteroaryl, cycloalkyl and a heterocyclic radical;

$R^{14}$ may also form a bond with $R^2$, thus forming a double bond between the carbon atoms respectively bearing the substituents $R^{14}$ and $R^2$; or alternatively $R^{14}$ forms, with $R^2$ and with the carbon atoms that bear them, a ring containing a total of 3, 4, 5, 6 or 7 carbon atoms, among which 1, 2 or 3 may be replaced with an atom chosen from nitrogen, oxygen and sulfur, the said ring possibly comprising one or more unsaturations in the form of (a) double bond(s), and being optionally substituted by one or more radicals, which may be identical or different, chosen from oxo, alkoxy, alkoxycarbonyl and alkylcarbonyloxy;

$R^{15}$ is chosen from hydrogen, a halogen atom, hydroxyl, thiol, carboxyl, alkyl, alkenyl, alkynyl, alkylcarbonyl, alkoxycarbonyl, alkoxy, alkenyloxy, alkynyloxy, aryloxy, cycloalkyloxy, heteroaryloxy, heterocyclyloxy, alkylthio, alkenylthio, alkynylthio, arylthio, cycloalkylthio, heteroarylthio, heterocyclylthio, aryl, heteroaryl, cycloalkyl and a heterocyclic radical;

$R^{14}$ and $R^{15}$ also possibly forming, together with the carbon atom that bears them, a cycloalkyl radical or a heterocyclic radical;

$R^{16}$ and $R^{17}$, which may be identical or different, are chosen, independently of each other, from hydrogen, a halogen atom, an alkyl, aryl, heteroaryl or cycloalkyl radical and a heterocyclic radical; or alternatively $R^{16}$ and $R^{17}$ form, together with the carbon atom that bears them, a cycloalkyl radical or a heterocyclic radical; and $R^{11}$ is chosen from hydrogen and an alkyl, aryl, arylalkyl, heteroaryl, heteroarylalkyl, cycloalkyl or cycloalkylalkyl radical, and any protecting group for an amine function;

with the restriction that when $R^3$, $R^2$ and $R^{14}$ each represent hydrogen, then $R^{15}$ is other than an alkyl radical, optionally substituted by aryl, heteroaryl, cycloalkyl and a heterocyclic radical;

and also the possible geometrical and/or optical isomers thereof, and possible tautomeric forms thereof;

the solvates and hydrates of these compounds;

and the possible salts thereof with a pharmaceutically acceptable acid or base, or alternatively the pharmaceutically acceptable prodrugs of these compounds.

Among the compounds (Ia) defined above, the compounds that will also be preferred are those of the family (Ib) belonging to formula (I) in which:

W represents a divalent radical chosen from the radicals:

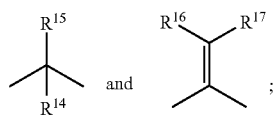

$R^1$ represents a phenyl radical, optionally substituted by 1, 2 or 3 groups chosen from cyano, nitro, phenyl, benzyl, alkyl, alkenyl containing from 2 to 4 carbon atoms, alkynyl containing from 2 to 4 carbon atoms, alkoxy, thiol —$SR^{13'}$, —$S(O)R^{13'}$ and —$S(O_2)R^{13'}$, and a halogen atom;

$R^2$ is chosen from hydrogen, a halogen atom, hydroxyl, thiol, optionally substituted alkyl, in particular benzyl, alkenyl containing from 2 to 4 carbon atoms, alkoxy, alkylthio and phenyl;

$R^3$ is chosen from hydrogen, a halogen atom, hydroxyl, thiol, optionally substituted alkyl, in particular benzyl, alkenyl containing from 2 to 4 carbon atoms, alkoxy, alkylthio and phenyl;

$R^2$ and $R^3$ together also possibly forming a group $=CR^{16}R^{17}$;

$R^4$ is chosen from hydroxyl, optionally substituted alkoxy, in particular benzyloxy, alkenyloxy containing from 2 to 4 carbon atoms, alkynyloxy containing from 2 to 4 carbon atoms, phenoxy, $-N(R^{12}R^{12'})$ and $-N(R^{12})OR^{13}$;

$R^{12}$ and $R^{12'}$, which may be identical or different, are chosen, independently of each other, from hydrogen, an optionally substituted alkyl radical, in particular benzyl, alkenyl containing from 2 to 4 carbon atoms, alkynyl containing from 2 to 4 carbon atoms, and phenyl;

$R^{13}$ is chosen from hydrogen, an optionally substituted alkyl radical, in particular benzyl, alkenyl containing from 2 to 4 carbon atoms, alkynyl containing from 2 to 4 carbon atoms, and phenyl;

$R^{13'}$ is chosen from an optionally substituted alkyl radical, in particular benzyl, alkenyl containing from 2 to 4 carbon atoms, alkynyl containing from 2 to 4 carbon atoms, phenyl and $-N(R^{12}R^{12'})$;

$R^{14}$ is chosen from hydrogen, a halogen atom, hydroxyl, thiol, optionally substituted alkyl, in particular benzyl, alkenyl containing from 2 to 4 carbon atoms, alkoxy, alkylthio and phenyl;

$R^{14}$ may also form a bond with $R^2$, thus forming a double bond between the carbon atoms respectively bearing the substituents $R^{14}$ and $R^2$;

$R^{15}$ is chosen from hydrogen, a halogen atom, hydroxyl, thiol, optionally substituted alkyl, in particular benzyl, alkenyl containing from 2 to 4 carbon atoms, alkoxy, alkylthio and phenyl;

$R^{16}$ is chosen from hydrogen, a halogen atom, hydroxyl, thiol, optionally substituted alkyl, in particular benzyl, alkenyl containing from 2 to 4 carbon atoms, alkoxy, alkylthio and phenyl; and $R^{17}$ represents a hydrogen atom;

with the restriction that when $R^3$, $R^2$ and $R^{14}$ each represent hydrogen, then $R^{15}$ is other than an alkyl radical, optionally substituted by aryl, heteroaryl, cycloalkyl and a heterocyclic radical;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

In the vast majority, the compounds (Ib) defined above show entirely advantageous inhibitory activity on kynurenine 3-hydroxylase. As a result, these compounds are most particularly preferred and simple to use for the preparation of antidiabetic medicaments.

According to another variant of the invention, this invention relates to the use of compounds of the family (Ic) with inhibitory activity on kynurenine 3-hydroxylase, for the preparation of a medicament for the prevention and/or treatment of diabetes. These compounds of family (Ic) have the general structure (I) as defined above, in which:

W represents the divalent radical:

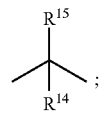

$R^1$ represents a radical chosen from linear or branched alkyl containing from 1 to 14 carbon atoms and optionally substituted, alkenyl, alkynyl, cycloalkyl, cycloalkenyl, a heterocyclic radical, an aryl radical and a heteroaryl radical;

$R^2$ represents hydrogen;

$R^3$ represents hydrogen;

$R^4$ is chosen from hydroxyl, alkoxy, alkenyloxy, alkynyloxy, aryloxy, heteroaryloxy, $-N(R^{12}R^{12'})$ and $-N(R^{12})OR^{13}$;

$R^{12}$ and $R^{12'}$, which may be identical or different, are chosen, independently of each other, from hydrogen and an alkyl, alkenyl, alkynyl, alkylcarbonyl, aryl or heteroaryl radical; or alternatively $R^{12}$ and $R^{12'}$ may form, together with the nitrogen atom to which they are attached, a monocyclic or bicyclic heterocyclic group containing a total of 5 to 10 atoms, among which 1, 2, 3 or 4 are chosen, independently of each other, from nitrogen, oxygen and sulfur, the said heterocyclic radical also optionally comprising 1, 2, 3 or 4 double bonds and optionally being substituted by one or more chemical groups, which may be identical or different, chosen from hydroxyl, halogen atom, alkyl, alkenyl, alkynyl, alkoxy, alkylthio, aryl, heteroaryl, heterocyclic radical and trifluoromethyl;

$R^{13}$ is chosen from hydrogen and an alkyl, alkenyl, alkynyl, aryl, heteroary, $-N(R^{12}R^{12'})$ or $-N(R^{12})OR^{13}$ radical;

$R^{14}$ represents hydrogen;

$R^{15}$ represents hydrogen;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

According to another variant, the invention relates to the use of compounds of the family (Id) with inhibitory activity on kynurenine 3-hydroxylase, for the preparation of a medicament for the prevention and/or treatment of diabetes, the said compounds (Id) having the general structure (I) as defined above, in which:

W represents the divalent radical:

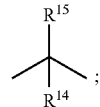

$R^1$ represents a radical chosen from linear or branched alkyl containing from 1 to 14 carbon atoms and optionally substituted, alkenyl, alkynyl, cycloalkyl, cycloalkenyl, a heterocyclic radical, an aryl radical and a heteroaryl radical;

$R^2$ represents hydrogen;

$R^3$ represents hydrogen;

$R^4$ is chosen from hydroxyl, alkoxy, alkenyloxy, alkynyloxy, aryloxy, heteroaryloxy, —$N(R^{12}R^{12'})$ and —$N(R^{12})OR^{13}$;

$R^{12}$ and $R^{12'}$, which may be identical or different, are chosen, independently of each other, from hydrogen and an alkyl, alkenyl, alkynyl, alkylcarbonyl, aryl or heteroaryl radical; or alternatively $R^{12}$ and $R^{12'}$ may form, together with the nitrogen atom to which they are attached, a monocyclic or bicyclic heterocyclic group containing a total of 5 to 10 atoms, among which 1, 2, 3 or 4 are chosen, independently of each other, from nitrogen, oxygen and sulfur, the said heterocyclic radical also optionally comprising 1, 2, 3 or 4 double bonds and optionally being substituted by one or more chemical groups, which may be identical or different, chosen from hydroxyl, halogen atom, alkyl, alkenyl, alkynyl, alkoxy, alkylthio, aryl, heteroaryl, heterocyclic radical and trifluoromethyl;

$R^{13}$ is chosen from hydrogen and an alkyl, alkenyl, alkynyl, aryl, heteroaryl, —$N(R^{12}R^{12'})$ or —$N(R^{12})OR^{13}$ radical;

$R^{14}$ represents hydrogen; and $R^{15}$ is chosen from hydroxyl, alkoxy, alkenyloxy, alkynyloxy, aryloxy, cycloalkyloxy, heteroaryloxy and heterocyclyloxy;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

Another preferred group of compounds consists of the compounds of family (Ie) with inhibitory activity on kynurenine 3-hydroxylase, which are useful for the preparation of a medicament for the prevention and/or treatment of diabetes, the said compounds (Ie) belonging to the general formula (I) as defined above, in which:

W represents the divalent radical:

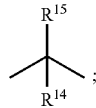

$R^1$ represents a radical chosen from linear or branched alkyl containing from 1 to 14 carbon atoms and optionally substituted, alkenyl, alkynyl, cycloalkyl, cycloalkenyl, a heterocyclic radical, an aryl radical and a heteroaryl radical;

$R^2$ and $R^{14}$ together form a bond, thus forming a double bond between the carbon atoms respectively bearing $R^2$ and $R^{14}$;

$R^3$ represents hydrogen;

$R^4$ is chosen from hydroxyl, alkoxy, alkenyloxy, alkynyloxy, aryloxy, heteroaryloxy, —$N(R^{12}R^{12'})$ and —$N(R^{12})OR^{13}$;

$R^{12}$ and $R^{12'}$, which may be identical or different, are chosen, independently of each other, from hydrogen and an alkyl, alkenyl, alkynyl, alkylcarbonyl, aryl or heteroaryl radical; or alternatively $R^{12}$ and $R^{12'}$ may form, together with the nitrogen atom to which they are attached, a monocyclic or bicyclic heterocyclic group containing a total of 5 to 10 atoms, among which 1, 2, 3 or 4 are chosen, independently of each other, from nitrogen, oxygen and sulfur, the said heterocyclic radical also optionally comprising 1, 2, 3 or 4 double bonds and optionally being substituted by one or more chemical groups, which may be identical or different, chosen from hydroxyl, halogen atom, alkyl, alkenyl, alkynyl, alkoxy, alkylthio, aryl, heteroaryl, heterocyclic radical and trifluoromethyl;

$R^{13}$ is chosen from hydrogen and an alkyl, alkenyl, alkynyl, aryl, heteroaryl, —$N(R^{12}R^{12'})$ or —$N(R^{12})OR^{13}$ radical; and $R^{15}$ represents hydrogen;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

According to another variant of the present invention, this invention relates to the use of compounds of family (If) with inhibitory activity on kynurenine 3-hydroxylase, which are useful for the preparation of a medicament for the prevention and/or treatment of diabetes, the said compounds (If) belonging to the general formula (I) as defined above, in which:

W represents the divalent radical:

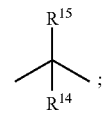

$R^1$ represents a radical chosen from linear or branched alkyl containing from 1 to 14 carbon atoms and optionally substituted, alkenyl, alkynyl, cycloalkyl, cycloalkenyl, a heterocyclic radical, an aryl radical and a heteroaryl radical;

$R^2$ and $R^{14}$ together form a bond, thus forming a double bond between the carbon atoms respectively bearing $R^2$ and $R^{14}$;

$R^3$ represents hydrogen;

$R^4$ is chosen from hydroxyl, alkoxy, alkenyloxy, alkynyloxy, aryloxy, heteroaryloxy, —$N(R^{12}R^{12'})$ and —$N(R^{12})OR^{13}$;

$R^{12}$ and $R^{12'}$, which may be identical or different, are chosen, independently of each other, from hydrogen and an alkyl, alkenyl, alkynyl, alkylcarbonyl, aryl or heteroaryl radical; or alternatively $R^{12}$ and $R^{12'}$ may form, together with the nitrogen atom to which they are attached, a monocyclic or bicyclic heterocyclic group containing a total of 5 to 10 atoms, among which 1, 2, 3 or 4 are chosen, independently of each other, from nitrogen, oxygen and sulfur, the said heterocyclic radical also optionally comprising 1, 2, 3 or 4 double bonds and optionally being substituted by one or more chemical groups, which may be identical or different, chosen from hydroxyl, halogen atom, alkyl, alkenyl, alkynyl, alkoxy, alkylthio, aryl, heteroaryl, heterocyclic radical and trifluoromethyl;

$R^{13}$ is chosen from hydrogen and an alkyl, alkenyl, alkynyl, aryl, heteroaryl, —$N(R^{12}R^{12'})$ or —$N(R^{12})OR^{13}$ radical; and $R^{15}$ is chosen from hydroxyl, alkoxy, alkenyloxy, alkynyloxy, aryloxy, cycloalkyloxy, heteroaryloxy and heterocyclyloxy;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

Among the compounds of the general formula (I), and according to another variant of the invention, the compounds are chosen from the family of compounds (Ig) consisting of:
4-(4'-methylcyclohexyl)-4-oxobutanoic acid;
2-hydroxy-4-(3',4'-difluorophenyl)-4-oxobutanoic acid;
2-methoxy-4-(3',4'-difluorophenyl)-4-oxobutanoic acid;
2-hydroxy-3-methyl-4-(3',4'-dichlorophenyl)-4-oxobutanoic acid;
2-hydroxy-3-phenyl-4-(3',4'-dichlorophenyl)-4-oxobutanoic acid;
2-hydroxy-3-benzyl-4-(3',4'-dichlorophenyl)-4-oxobutanoic acid;
2-methyl-4-(3',4'-dichlorophenyl)-4-oxobutanoic acid;
2-methyl-4-(3',4'-difluorophenyl)-4-oxobutanoic acid;
2-chloro-4-(3',4'-dichlorophenyl)-4-oxobutanoic acid;
2-chloro-4-(3',4'-difluorophenyl)-4-oxobutanoic acid;
2-fluoro-4-(3',4'-dichlorophenyl)-4-oxobutanoic acid;
2-fluoro-4-(3',4'-difluorophenyl)-4-oxobutanoic acid;
2-thiomethyl-4-(3',4'-dichlorophenyl)-4-oxobutanoic acid;
2-methylidene-4-(3',4'-dichlorophenyl)-4-oxobutanoic acid;
2-phenyl-4-(3',4'-dichlorophenyl)-4-oxobutanoic acid;
2-benzyl-4-(3',4'-dichlorophenyl)-4-oxobutanoic acid;
3-methyl-4-(3',4'-dichlorophenyl)-4-oxobutanoic acid;
3-phenyl-4-(3',4'-dichlorophenyl)-4-oxobutanoic acid;
3-benzyl-4-(3',4'-dichlorophenyl)-4-oxobutanoic acid;
methyl (R,S)-2-hydroxy-4-(3',4'-dichlorophenyl)-4-oxobutanoate;
methyl (R,S)-2-benzyl-4-(3',4'-dichlorophenyl)-4-oxobutanoate;
4-(3'-fluorophenyl)-4-oxo-2-butenoic acid;
4-(3'-chlorophenyl)-4-oxo-2-butenoic acid;
4-(3'-nitrophenyl)-4-oxo-2-butenoic acid;
4-(3'-fluoro-4'-methoxyphenyl)-4-oxo-2-butenoic acid;
2-methyl-4-(3',4'-dichlorophenyl)-4-oxo-2-butenoic acid;
3-methyl-4-(3',4'-dichlorophenyl)-4-oxo-2-butenoic acid;
3-phenyl-4-(3',4'-dichlorophenyl)-4-oxo-2-butenoic acid;
3-benzyl-4-(3',4'-dichlorophenyl)-4-oxo-2-butenoic acid;
2,3-dimethyl-4-(3',4'-dichlorophenyl)-4-oxo-2-butenoic acid;
2-hydroxy-4-(3'-chlorophenyl)-4-oxo-2-butenoic acid;
2-hydroxy-4-(3'-fluorophenyl)-4-oxo-2-butenoic acid;
2-hydroxy-4-(3',4'-dichlorophenyl)-4-oxo-2-butenoic acid;
2-hydroxy-4-(3',4'-difluorophenyl)-4-oxo-2-butenoic acid; and
2-hydroxy-4-(3'-chloro-4'-methoxyphenyl)-4-oxo-2-butenoic acid;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

According to another variant of the invention, a family of compounds (Ih) having the abovementioned general structure (I) is defined, for which:

W represents the divalent radical:

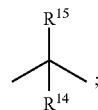

$R^1$, $R^2$, $R^3$, $R^4$, $R^{12}$, $R^{12'}$, $R^{13}$ and $R^{14}$ are as defined above; and $R^{15}$ is chosen from a thiol, alkylthio, alkenylthio, alkynylthio, arylthio, cycloalkylthio, heteroarylthio or heterocyclylthio radical;

with the restriction that when $R^2$, $R^3$ and $R^{14}$ each represent hydrogen, then $R^{15}$ cannot represent a thiol or alkylthio radical;

and also the possible geometrical and/or optical isomers thereof, and the is possible tautomeric forms thereof;

the solvates and hydrates of these compounds;

and also the possible salts thereof with a pharmaceutically acceptable acid or base, or alternatively the pharmaceutically acceptable prodrugs of these compounds.

The compounds of family (Ih) are novel and, in this respect, form another subject of the present invention. Furthermore, the compounds of family (Ih) have entirely noteworthy hypoglycaemiant properties and, in this respect, are useful in the treatment and/or prevention of diabetes and its complications.

The compounds of family (Ih) are consequently also useful for the preparation of a medicament for the prevention and/or treatment of diabetes and its complications.

In addition, the compounds of family (Ih) show inhibitory activity on kynurenine 3-hydroxylase that may be linked to the observed antidiabetic activity.

A preferred subfamily of the compounds of the family (Ih) consists of the compounds of the family (Ii) belonging to the general formula (I) in which:

W represents the divalent radical:

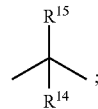

$R^1$ represents an aryl radical;

$R^2$ represent hydrogen, or forms a bond with $R^{14}$;

$R^3$ represents hydrogen;

$R^4$ is chosen from hydroxyl, alkoxy, alkenyloxy, alkynyloxy, aryloxy, heteroaryloxy, —N($R^{12}R^{12'}$) and —N($R^{12}$)O$R^{13}$;

$R^{12}$ and $R^{12'}$, which may be identical or different, are chosen, independently of each other, from hydrogen and an alkyl, alkenyl, alkynyl, alkylcarbonyl, aryl or heteroaryl radical; or alternatively $R^{12}$ and $R^{12'}$ may form, together with the nitrogen atom to which they are attached, a monocyclic or bicyclic heterocyclic group containing a total of 5 to 10 atoms, among which 1, 2, 3 or 4 are chosen, independently of each other, from nitrogen, oxygen and sulfur, the said heterocyclic radical also optionally comprising 1, 2, 3 or 4 double bonds and optionally being substituted by one or more chemical groups, which may be identical or different, chosen from hydroxyl, halogen atom, alkyl, alkenyl, alkynyl, alkoxy, alkylthio, aryl, heteroaryl, heterocyclic radical and trifluoromethyl;

$R^{13}$ is chosen from hydrogen and an alkyl, alkenyl, alkynyl, aryl, heteroaryl, —N($R^{12}R^{12'}$) or —N($R^{12}$)O$R^{13}$ radical;

$R^{14}$ represents hydrogen, or forms a bond with $R^2$; and $R^{15}$ represents an arylthio radical;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

Among the compounds of family (Ii) that are also preferred are the compounds of family (Ij) corresponding to the general formula (I), in which:

W represents the divalent radical:

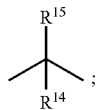

$R^1$ represents a phenyl radical;
$R^2$ represents hydrogen;
$R^3$ represents hydrogen;
$R^4$ is chosen from hydroxyl and an alkoxy radical;
$R^{14}$ represents hydrogen; and
$R^{15}$ represents a phenylthio radical;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

By way of illustration, examples of compounds of family (Ih) are:

compound Ih-1:
2-(2'-naphthylthio)-4-phenyl-4-oxobutanoic acid;
compound Ih-2:
2-phenylthio-4-phenyl-4-oxobutanoic acid;
compound Ih-3:
2-(4'-fluorophenylthio)-4-phenyl-4-oxobutanoic acid;
compound Ih-4:
2-(4'-chlorophenylthio)-4-phenyl-4-oxobutanoic acid;
compound Ih-5:
2-(4'-methylphenylthio)-4-phenyl-4-oxobutanoic acid;
compound Ih-6:
2-(4'-methoxyphenylthio)-4-phenyl-4-oxobutanoic acid;
compound Ih-7:
2-cyclohexylthio-4-phenyl-4-oxobutanoic acid;
compound Ih-8:
2-benzylthio-4-phenyl-4-oxobutanoic acid;
compound Ih-9:
ethyl 2-phenylthio-4-phenyl-4-oxobutanoate;
compound Ih-10:
ethyl 2-(4'-fluorophenylthio)-4-phenyl-4-oxobutanoate;
compound Ih-11:
ethyl 2-(4'-chlorophenylthio)-4-phenyl-4-oxobutanoate;
compound Ih-12:
ethyl 2-(4'-methylphenylthio)-4-phenyl-4-oxobutanoate;
compound Ih-13:
ethyl 2-(4'-methoxyphenylthio)-4-phenyl-4-oxobutanoate;
compound Ih-14:
ethyl 2-(2'-naphthylthio)-4-phenyl-4-oxobutanoate;
compound Ih-15:
ethyl 2-cyclohexylthio-4-phenyl-4-oxobutanoate;
compound Ih-16:
ethyl 2-benzylthio-4-phenyl-4-oxobutanoate;
compound Ih-17:
2-phenylthio-4-(4'-methoxyphenyl)-4-oxobutanoic acid;
compound Ih-18:
2-(4'-fluorophenylthio)-4-(4'-methoxyphenyl)-4-oxobutanoic acid;
compound Ih-19:
2-(4'-chlorophenylthio)-4-(4'-methoxyphenyl)-4-oxobutanoic acid;
compound Ih-20:
2-(4'-methylphenylthio)-4-(4'-methoxyphenyl)-4-oxobutanoic acid;
compound Ih-21:
2-(4'-methoxyphenylthio)-4-(4'-methoxyphenyl)-4-oxobutanoic acid;
compound 1h-22:
2-(2'-naphthylthio)-4-(4'-methoxyphenyl)-4-oxobutanoic acid;
compound Ih-23:
2-cyclohexylthio-4-(4'-methoxyphenyl)-4-oxobutanoic acid;
compound Ih-24:
2-benzylthio-4-(4'-methoxyphenyl)-4-oxobutanoic acid;
compound 1 h-25:
2-phenylthio-4-(4'-chlorophenyl)-4-oxobutanoic acid;
compound Ih-26:
2-(4'-fluorophenylthio)-4-(4'-chlorophenyl)-4-oxobutanoic acid;
compound Ih-27:
2-(4'-chlorophenylthio)-4-(4'-chlorophenyl)-4-oxobutanoic acid;
compound Ih-28:
2-(4'-methylphenylthio)-4-(4'-chlorophenyl)-4-oxobutanoic acid;
compound Ih-29:
2-(4'-methoxyphenylthio)-4-(4'-chlorophenyl)-4-oxobutanoic acid;
compound Ih-30:
2-(2'-naphthylthio)-4-(4'-chlorophenyl)-4-oxobutanoic acid;

and 2-carboxymethylthio-4-phenyl-4-oxobutanoic acid (f);

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

According to one particular aspect of the invention, among the different variants of the formula (I) above that are preferred are the compounds for which, when $R^2=R^3=H$, W is other than —CH(CH$_2$—X)— in which X=alkyl, aryl, cycloalkyl, pyridyl, pyrimidyl, pyrrolyl, furyl, thienyl, tetrahydrofuryl, tetrahydropyranyl, piperidyl or pyrrolidinyl, which are optionally substituted.

According to another particular aspect of the invention, the compounds of the formula (I) are different from:

racemic 2-benzyl-4-(4-methoxyphenyl)-4-oxobutanoic acid and the R and S isomers thereof;

racemic 2-benzyl-4-(4-fluorophenyl)-4-oxobutanoic acid and the R and S isomers thereof;

2-cyclohexylmethyl-4-(4-methoxyphenyl)-4-oxobutanoic acid;

2-benzyl-4-phenyl-4-oxobutanoic acid;

2-(β-naphthylmethyl)-4-phenyl-4-oxobutanoic acid;

2-benzyl-4-(β-naphthyl)-4-oxobutanoic acid;

2-[(4-chlorophenyl)methyl]-4-(4-methoxyphenyl)-4-oxobutanoic acid;
2-benzyl-4-(4-methylphenyl)-4-oxobutanoic acid;
4-(4-fluorophenyl)-2-[(4-methoxyphenyl)methyl]-4-oxobutanoic acid;
2-benzyl-4-(3,4-methylenedioxyphenyl)-4-oxobutanoic acid;
2-benzyl-4-cyclohexyl-4-oxobutanoic acid;
4-phenyl-2-[(tetrahydrofur-2-yl)methyl]-4-oxobutanoic acid.

According to one particularly advantageous aspect according to the present invention, among the variants of the formula (I)° above that are preferred are the compounds for which $R^1$ represents an aryl radical or a heteroaryl radical.

Among the compounds of the formula (II) defined above that are preferred are the compounds of the family (IIa) corresponding to the general formula (II) in which:

$R^5$, $R^6$, $R^7$ and $R^8$ are as defined above;

$R^9$ represents hydrogen; and $R^{10}$ is chosen from a phenyl radical, optionally substituted in position 3 and/or 4 with an alkyl or alkoxy radical, preferably methyl or methoxy, and a naphthyl radical;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

Another family (IIb) of compounds of the formula (II) is represented by the compounds of the general formula (II) in which:

$R^5$, $R^6$, $R^7$ and $R^8$, which may be identical or different, are chosen, independently of each other, from hydrogen, a halogen atom, a nitro radical and a trifluoromethyl radical;

the radicals $R^6$ and $R^7$ also possibly forming, together with the carbon atoms to which they are attached, a benzene ring, optionally substituted by one or more groups, which may be identical or different, chosen from a halogen atom and a trifluoromethyl, nitro or alkoxy radical; and $R^9$ and $R^{10}$ are as defined above;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

According to one preferred variant of the invention, the compounds of the formula (II) are chosen from the list consisting of:

4-methoxy-N-(4-naphthalen-2-ylthiazol-2-yl)benzenesulfonamide;
4-amino-N-[4-(3-nitrophenyl)thiazol-2-yl]benzenesulfonamide;
4-methyl-N-[4-(3-nitrophenyl)thiazol-2-yl]benzenesulfonamide;
3,4-dimethoxy-N-[4-(3-nitrophenyl)thiazol-2-yl]benzenesulfonamide;
4-methoxy-N-[4-(3-nitrophenyl)thiazol-2-yl]benzenesulfonamide;
2-naphthalenesulfonic acid [4-(3-nitrophenyl)thiazol-2-yl]benzenesulfonamide;
N-[4-(2-fluoro-5-trifluoromethylphenyl)thiazol-2-yl]-4-methylbenzenesulfonamide;
N-[4-(3-fluoro-5-trifluoromethylphenyl)thiazol-2-yl]-4-methylbenzenesulfonamide;
4-methyl-N-[4-(4-nitrophenyl)thiazol-2-yl]benzenesulfonamide;
4-amino-N-[4-(2-fluoro-5-trifluoromethylphenyl)thiazol-2-yl]benzenesulfonamide; and
3,4-dimethoxy-N-[4-(2-fluoro-5-trifluoromethylphenyl)thiazol-2-yl]-benzenesulfenamide;

and also the possible geometrical and/or optical isomers thereof, and the possible tautomeric forms thereof;

the solvates and hydrates of these compounds;

and also the possible salts thereof with a pharmaceutically acceptable acid or base, or alternatively the pharmaceutically acceptable prodrugs of these compounds.

Among the compounds of the general formulae (I) and (II) and variants thereof discussed above, compounds with substantial inhibitory activity on kynurenine 3-hydroxylase as defined above are particularly preferred.

The compounds of the formulae (I) and (II) defined above are useful for the preparation of medicaments or pharmaceutical compositions for the prevention and/or treatment of diabetes and its complications.

The pharmaceutical compositions thus comprise as active principle a pharmacologically effective amount of at least one compound of the formula (I) or of the formula (II), alone or in combination with one or more fillers, vehicles, colorants or sweeteners, i.e. any suitable and pharmaceutically acceptable non-toxic, inert excipient usually used in the production of pharmaceutical compositions.

The pharmaceutical compositions thus obtained will be in various forms, the most advantageous being gel capsules, suppositories, injectable or drinkable solutions, patches, plain, sugar-coated, film-coated or sublingual tablets, sachets, packets, lozenges, creams, ointments, dermal gels, aerosols, etc.

The working dose may be adapted according to the nature and severity of the pathology to be treated, the administration route and also the patient's age and weight. In general, the unit dose will range between 5 mg and 2000 mg per day, in one or more dosage intakes, advantageously between 10 mg and 1000 mg, for example between 50 mg and 800 mg.

It has been discovered, surprisingly, that the kynurenine 3-hydroxylase inhibitors have the twofold activity of controlling the secretion of both glucagon and insulin. Specifically, in the absence of glucose, the secretion of glucagon is stimulated whereas that of insulin is not. In the presence of glucose, the secretion of insulin is potentiated whereas the secretion of glucagon remains normally inhibited.

Such a dual activity affords a considerable improvement over the processes for the treatment of diabetes currently used. Specifically, the risks of hypoglycaemia are very greatly reduced, or even virtually nonexistent, even when the prescribed doses and/or number of administrations are exceeded or have been poorly controlled.

The present invention consequently also relates to a process for the treatment of diabetes, which minimises or eliminates the risk of hypoglycaemia, the said process consisting in administering a pharmaceutically effective dose of one or more compounds that inhibit kynurenine 3-hydroxylase of the formula (I) or of the formula (II) as defined above.

Among the compounds of the formula (I) that have inhibitory activity on kynurenine 3-hydroxylase, non-limiting examples that may be mentioned include:

4-(3',4'-dichlorophenyl)-4-oxobutanoic acid;
4-(3',4'-difluorophenyl)-4-oxobutanoic acid;
methyl 4-(3',4'-dichlorophenyl)-4-oxobutanoate;
(R,S)-2-hydroxy-4-(3'-chlorophenyl)-4-oxobutanoic acid;
(R,S)-2-hydroxy-4-(3'-fluorophenyl)-4-oxobutanoic acid;
(R,S)-2-hydroxy-4-(3'-nitrophenyl)-4-oxobutanoic acid;
(R,S)-2-hydroxy-4-(3',4'-dichlorophenyl)-4-oxobutanoic acid;
(S)-2-hydroxy-4-(3',4'-dichlorophenyl)-4-oxobutanoic acid;
(R)-2-hydroxy-4-(3',4'-dichlorophenyl)-4-oxobutanoic acid;
methyl (R,S)-2-hydroxy-4-(3',4'-dichlorophenyl)-4-oxobutanoate;
(R,S)-2-hydroxy-4-(3',4'-difluorophenyl)-4-oxobutanoic acid;
(R,S)-2-methoxy-4-(3',4'-difluorophenyl)-4-oxobutanoic acid;
(R,S)-2-methoxy-4-(3',4'-dichlorophenyl)-4-oxobutanoic acid;
(R,S)-2-methyl-4-(3',4'-dichlorophenyl)-4-oxobutanoic acid;
(R,S)-3-methyl-4-(3',4'-dichlorophenyl)-4-oxobutanoic acid;
2-hydroxy-3-benzyl-4-(3',4'-dichlorophenyl)-4-oxobutanoic acid;
(R,S)-2-methyl-4-(3',4'-difluorophenyl)-4-oxobutanoic acid;
(R,S)-2-chloro-4-(3',4'-dichlorophenyl)-4-oxobutanoic acid;
(R,S)-2-methylidene-4-(3',4'-dichlorophenyl)-4-oxobutanoic acid;
(R,S)-3-phenyl-4-(3',4'-dichlorophenyl)-4-oxobutanoic acid;
methyl (R,S)-2-benzyl-4-(3',4'-dichlorophenyl)-4-oxobutanoate;
(R,S)-2-phenyl-4-(3',4'-dichlorophenyl)-4-oxobutanoic acid;
(R,S)-2-benzyl-4-(3',4'-dichlorophenyl)-4-oxobutanoic acid;
(E)-4-(3',4'-dichlorophenyl)-4-oxo-2-butenoic acid;
(E)-4-(3',4'-difluorophenyl)-4-oxo-2-butenoic acid;
(E)-4-(3'-fluorophenyl)-4-oxo-2-butenoic acid;
(E)-4-(3'-chlorophenyl)-4-oxo-2-butenoic acid;
(E)-4-(3'-nitrophenyl)-4-oxo-2-butenoic acid;
(E)-2-methyl-4-(3',4'-dichlorophenyl)-4-oxo-2-butenoic acid;
3-methyl-4-(3',4'-dichlorophenyl)-4-oxo-2-butenoic acid;
3-benzyl-4-(3',4'-dichlorophenyl)-4-oxo-2-butenoic acid;
(E)-2-hydroxy-4-(3'-chlorophenyl)-4-oxo-2-butenoic acid;
(E)-2-hydroxy-4-(3'-fluorophenyl)-4-oxo-2-butenoic acid;
(E)-2-hydroxy-4-(4'-chlorophenyl)-4-oxo-2-butenoic acid;
(E)-2-hydroxy-4-(3',4'-dichlorophenyl)-4-oxo-2-butenoic acid;
(E)-2-hydroxy-4-(3',4'-difluorophenyl)-4-oxo-2-butenoic acid;
methyl (E)-2-hydroxy-4-(3',4'-dichlorophenyl)-4-oxo-2-butenoate; and
ethyl (E)-2-hydroxy-4-(3',4'-dichlorophenyl)-4-oxo-2-butenoate;
and also the possible geometrical and/or optical isomers thereof, and the possible tautomeric forms thereof;
the solvates and hydrates of these compounds;

and also the possible salts thereof with a pharmaceutically acceptable acid or base, or alternatively the pharmaceutically acceptable prodrugs of these compounds.

The invention also relates to a process for the prevention or treatment of diabetes and/or its complications, comprising the administration, to a patient requiring it, of a dose of one or more compounds that inhibit kynurenine 3-hydroxylase of the formula (I) or of the formula (II) defined above, such that it produces a substantial inhibition of kynurenine 3-hydroxylase in the patient.

In particular, the process defined above allows the prevention of diabetes, especially in the case of patients presenting the characteristics of the diabetes pathology, without this pathology yet having been declared. The criteria for diagnosing this pathology are defined, for example, in *Diabetes Care*, vol. 25, suppl. 1, January 2002.

Among the complications that may be mentioned especially are arterial hypertension, diabetes-related inflammatory processes, macroangiopathy, microangiopathy, diabetic nephropathy, peripheral diabetic neuropathy and retinopathy of diabetic origin.

As mentioned previously, the compounds of the formulae (I) and (II) defined above have been found to be useful in the prevention and/or treatment of diabetes and its complications, according to a mode of action that is hitherto unknown in this therapeutic field.

The invention also relates to a process for manufacturing medicaments for the treatment and/or prevention of diabetes, in particular non-insulin-dependent diabetes, and its complications, by inhibiting kynurenine 3-hydroxylase, in which at least one compound of the formula (I) or (II) is subjected to an in vitro test of inhibition of kynurenine 3-hydroxylase, and the molecules responding positively to the said tests are then conditioned in the form of a pharmaceutical composition, optionally with addition of a pharmaceutically acceptable filler or vehicle.

Finally, the invention also relates to a process for screening candidate compounds for activity in the prevention or treatment of diabetes, and especially non-insulin-dependent diabetes or its complications, by inhibiting kynurenine 3-hydroxylase, the said candidates not corresponding to formula (I) or (II), in which process the candidate compounds are subjected to an in vitro test of inhibition of kynurenine 3-hydroxylase, and the candidate that has responded positively to this test is selected.

Among the candidates that will be preferred are the compounds already known as having antidiabetic activity.

The examples that follow illustrate, without placing any limitation of any kind on the invention, some of the subjects of the invention, in particular the preparation processes and the activities of some of the compounds described above in antidiabetic activity tests and tests of inhibition of kynurenine 3-hydroxylase.

PREPARATION EXAMPLE

Preparation of 2-(2'-naphthylthio)-4-phenyl-4-oxobutanoic acid (compound Ih-1)

7.04 g (0.04 mol) of commercial 3-benzoylacrylic acid are dissolved in 90 mL of methylene chloride. 2-Naphthalenethiol (0.04 mol; 1 equivalent) is then added. The reaction medium is left for 20 hours at 20° C. and then concentrated under vacuum. The crude solid product isolated is then triturated from isopropyl ether, filtered off by suction and recrystallised from isopropyl ether.

Isolated weight: 5.55 g; yield=41%; melting point=146-149° C. (capillary melting point).

Proton NMR (200 MHz, solvent: deuterated DMSO): 3.74 ppm, multiplet, 2H, 4.43 ppm, broad singlet, 1H, 7.9 ppm, multiplet, 12H arom.; 12.9 ppm, COOH).

Infrared spectrometry (cm$^{-1}$): 1702.8; 1680.7; 1595.0; 1435.2; 1326.6; 1217.6.

TLC Analysis:

silica, eluent: methylcyclohexane, ethyl acetate, acetic acid (50/45/5): Rf: 0.53.

The compounds of the family (Ih) as defined above were prepared according to a similar process.

Preparation of ethyl 2-(4-methoxyphenylthio)-4-phenyl-4-oxobutanoate (compound Ih-13)

0.408 g of commercial ethyl benzoylacrylate (0.002 mol) is dissolved in 6 ml of methylene chloride in a round-bottomed flask under argon. 0.280 g (1 equivalent) of 4-methoxythiophenol is then added.

The reaction medium is left at 20° C. for 72 hours and then concentrated under vacuum.

The crude oil isolated is then purified on a column of silica (eluent: 90/10 cyclohexane/ethyl acetate).

Isolated weight: 0.390 g; yield=56.6%; oil.

Proton NMR (200 MHz, solvent: deuterated chloroform): 1.06 ppm, triplet, 3H, 3.41 ppm, multiplet, 2H, 3.66 ppm, singlet, 3H, 4.01 ppm, multiplet, 3H, 6.72 ppm, doublet, 2H arom.; 7.32 ppm, multiplet, 5H arom.; 7.78 ppm, doublet, 2H arom.

Infrared spectrometry (cm$^{-1}$): 1730.6; 1685.1; 1493.9; 1448.8; 1287.6; 1248.21; 1213.6.

The ethyl ester compounds of family Ih as defined above were prepared according to a similar process.

The compounds of family Ih are collated in Tables I 1-4 below. The purities were determined by HPLC/MS.

TABLE I-1

Compounds Ih

| R—SH | Number | Mass | Purity (%) | Yield (%) | m.p. (° C.); (solvent*) |
|---|---|---|---|---|---|
| 2-naphthyl-SH | 1h | 336.41 | 99 | 81.1 | 146-149 (isopropyl ether) |
| phenyl-SH | 2h | 286.35 | 99 | 67.6 | 132-135 (ethanol at 85) |
| 4-F-phenyl-SH | 3h | 304.34 | 99 | 68.4 | 114-116 (isopropyl ether) |

TABLE I-1-continued

Compounds Ih

| R—SH | Number | Mass | Purity (%) | Yield (%) | m.p. (° C.); (solvent*) |
|---|---|---|---|---|---|
| 4-Cl-phenyl-SH | 4h | 320.8 | 99 | 72.5 | 140-142 (ethanol 85) |
| 4-CH₃-phenyl-SH | 5h | 300.38 | 99 | 66 | 132-134 (ethanol 95) |
| 4-CH₃O-phenyl-SH | 6h | 316.38 | 99 | 77.2 | 116-118 (ethanol 50) |
| cyclohexyl-SH | 7h | 292.4 | 99 | 6.8 | 117 (ethanol 50) |
| benzyl-SH | 8h | 300.38 | 99 | 52.7 | 143-146 (ethanol 95) |

*solvent recrystallisation

TABLE I-2

Compounds Ih

| R—SH | Number | Mass | Purity (%) | Yield (%) | m.p. (° C.); (solvent*) |
|---|---|---|---|---|---|
| phenyl-SH | 9h | 341.41 | 99 | 33 | oil |
| 4-F-phenyl-SH | 10h | 332.4 | 97.4 | 24 | oil |
| 4-Cl-phenyl-SH | 11h | 348.85 | 95.2 | 19.8 | oil |

TABLE I-2-continued

Compounds Ih

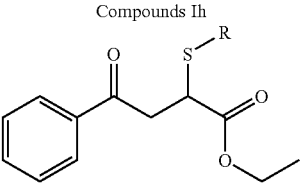

| R—SH | Number | Mass | Purity (%) | Yield (%) | m.p. (° C.); (solvent*) |
|---|---|---|---|---|---|
| 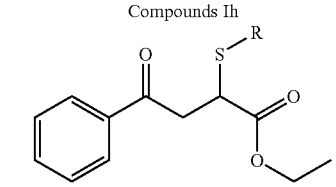 | 12h | 328.43 | 94.4 | 24.2 | oil |
| 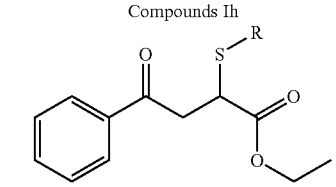 | 13h | 344.43 | 95.7 | 56.6 | oil |
| 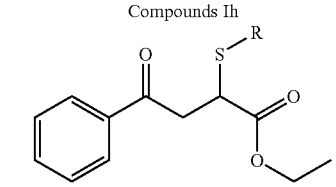 | 14h | 364.47 | 94 | 9.6 | oil |
| 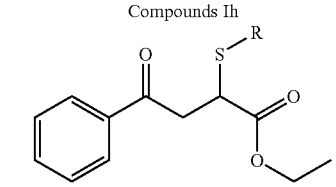 | 15h | 320.42 | 99 | 75.8 | oil |
| 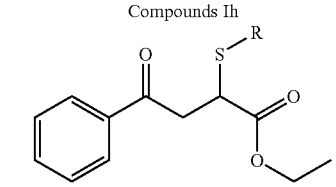 | 16h | 328.43 | 99 | 41.2 | oil |

TABLE I-3

Compounds Ih

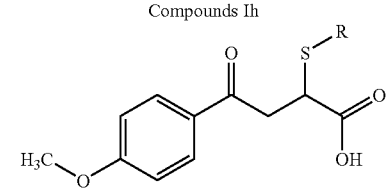

| R—SH | Number | Mass | Purity (%) | Yield (%) | m.p. (° C.); (solvent*) |
|---|---|---|---|---|---|
| 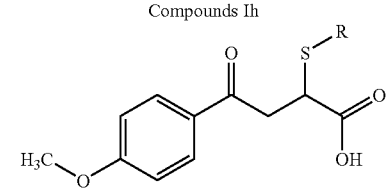 | 17h | 316.38 | 99 | 70.4 | 121-125 (ethanol 50) |
| 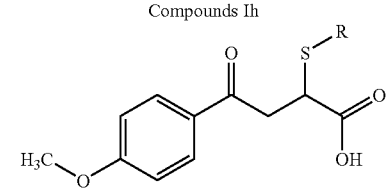 | 18h | 334.37 | 98.2 | 51.3 | 108-110 (ethanol 50) |
| 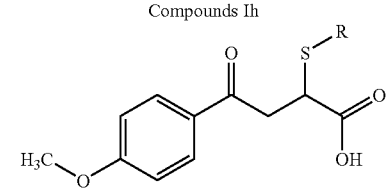 | 19h | 350.82 | 99 | 68 | 120-121 (ethanol 50) |

TABLE I-3-continued

Compounds Ih

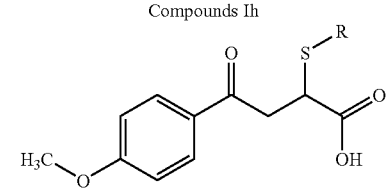

| R—SH | Number | Mass | Purity (%) | Yield (%) | m.p. (° C.); (solvent*) |
|---|---|---|---|---|---|
| 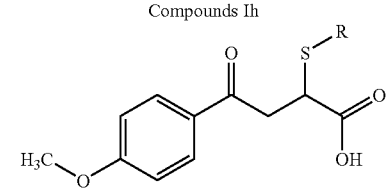 | 20h | 330.41 | 99 | 23.2 | 137-141 (ethanol 70) |
| 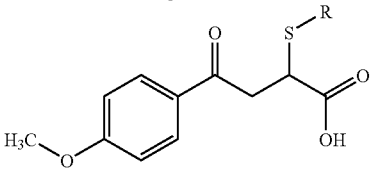 | 21h | 346.4 | 99 | 68 | 137-140 (ethanol 70) |
| 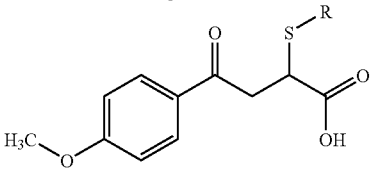 | 22h | 366.44 | 99 | 87.4 | 167-169 (ethanol 50) |
| 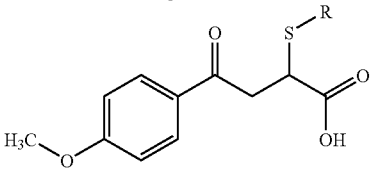 | 23h | 322.43 | 96.7 | 30.4 | 120-122 (ethanol 50) |
| 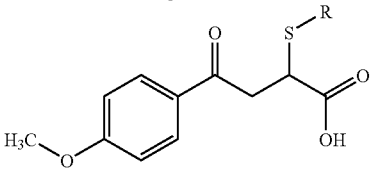 | 24h | 330.41 | 91.8 | 72.5 | 105-109 (ethanol 50) |

*solvent recrystallisation

TABLE I-4

Compounds Ih

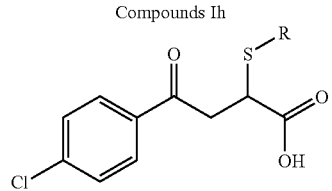

| R—SH | Number | Mass | Purity (%) | Yield (%) | m.p. (° C.); (solvent*) |
|---|---|---|---|---|---|
| 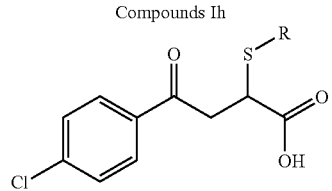 | 25h | 320.8 | 98.5 | 78.5 | 166-169 (ethanol 85) |
| 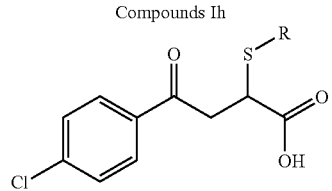 | 26h | 338.79 | 98.6 | 81.2 | 140-141 (ethanol 85) |
| 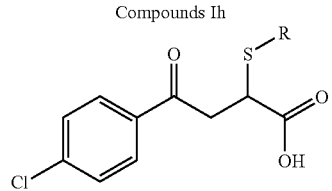 | 27h | 355.24 | 97.8 | 82.8 | 154-156 (ethanol 85) |

TABLE I-4-continued

Compounds Ih

[Structure: 4-chlorophenyl-C(O)-CH2-CH(SR)-C(O)OH]

| R—SH | Number | Mass | Purity (%) | Yield (%) | m.p. (° C.); (solvent*) |
|---|---|---|---|---|---|
| 4-methylphenyl-SH | 28h | 334.82 | 99 | 62.9 | 151-153 (ethanol 85) |
| 4-methoxyphenyl-SH | 29h | 350.82 | 99 | 54.2 | 117-119 (ethanol 70) |
| 2-naphthyl-SH | 30h | 370.86 | 96.6 | 82.7 | 141-145 (isopropyl ether) |

*solvant recrystallisation

Study of the Inhibitory Activity on Kynurenine 3-hydroxylase in Rat Liver

Experimental Protocol

Rat livers are homogenised (1:8 weight/volume) in a buffer solution comprising:
0.25 M sucrose
50 mM pH 7.4 Tris;
1 mM EDTA; and
1 mM DTT.

The homogenates are centrifuged for 10 minutes at 12 000 rpm. The pellets are resuspended in the buffer solution described above (1:2 weight/volume).

The kynurenine 3-hydroxylase inhibition is determined by incubating 10 μL of the homogenate with NADPH (2 mM), kynurenine (100 μM) and various concentrations of the test compounds in a final volume of 100 μL at 37° C. for 5 minutes.

The compounds are tested at concentrations of between 1 μM and 300 μM. 3,4-Dimethoxy-N-[4-(3-nitrophenyl)thiazol-2-yl]benzenesulfonamide is a compound from the company Hoffmann-LaRoche (Basle, see *J. Med. Chem.*, 40 (1997), 4738). 30H-Kynurenine was tested according to the protocol described by Carpendo et al. (*Neuroscience*, 61 (1994), 237-244).

Results:

Each of the experiments is repeated once and the $IC_{50}$ values (in μmol/L) are calculated and given in the form of a mean of these two experiments.

By way of example, (R)-2-benzyl-4-(4-fluorophenyl)-4-oxobutanoic acid (compound i) has an $IC_{50}$ value of 1·.·0.2 μmol/L, whereas 3,4-dimethoxy-N-[4-(3-nitrophenyl) thiazol-2-yl]benzenesulfonamide (compound k) has an $IC_{50}$ value of 10±2.1 μmol/L.

Results concerning representative examples of family Ih are given in Table II below, in which is indicated the measurement of the percentage of remaining kynurenine 3-hydroxylase activity relative to the control (100%).

| R—SH | Ih | Kynurenine 3-hydroxylase inhibition |
|---|---|---|
| 2-naphthyl-SH | Ih-1 | 23.2 |
| phenyl-SH | Ih-2 | 70.4 |
| 4-fluorophenyl-SH | Ih-3 | 50.4 |
| 4-chlorophenyl-SH | Ih-4 | 34.8 |
| 4-methylphenyl-SH | Ih-5 | 45.4 |
| cyclohexyl-SH | Ih-7 | 81.3 |
| benzyl-SH | Ih-8 | 68.6 |
| phenyl-SH (ethyl ester) | Ih-9 | 80.8 |
| 4-fluorophenyl-SH (ethyl ester) | Ih-10 | 66.7 |

-continued

| R—SH | Ih | Kynurenine 3-hydroxylase inhibition |
|---|---|---|
| 4-chlorophenyl-SH | Ih-11 | 44.6 |
| 4-methylphenyl-SH | Ih-12 | 63.3 |
| 4-methoxyphenyl-SH | Ih-13 | 55.2 |
| 2-naphthyl-SH | Ih-14 | 30.0 |
| cyclohexyl-SH | Ih-15 | 95.0 |
| benzyl-SH | Ih-16 | 84.4 |

[Structure: 4-methoxyphenyl C(=O)CH₂CH(S-R)C(=O)OH]

| R—SH | Ih | Kynurenine 3-hydroxylase inhibition |
|---|---|---|
| phenyl-SH | Ih-17 | 16.0 |
| 4-fluorophenyl-SH | Ih-18 | 6.6 |
| 4-chlorophenyl-SH | Ih-19 | 4.1 |
| 4-methylphenyl-SH | Ih-20 | 13.3 |
| 4-methoxyphenyl-SH | Ih-21 | 17.4 |

-continued

| R—SH | Ih | Kynurenine 3-hydroxylase inhibition |
|---|---|---|
| 2-naphthyl-SH | Ih-22 | 8.5 |
| cyclohexyl-SH | Ih-23 | 38.1 |
| benzyl-SH | Ih-24 | 18.9 |

[Structure: 4-chlorophenyl C(=O)CH₂CH(S-R)C(=O)OH]

| R—SH | Ih | Kynurenine 3-hydroxylase inhibition |
|---|---|---|
| phenyl-SH | Ih-25 | 67.6 |
| 4-fluorophenyl-SH | Ih-26 | 55.5 |
| 4-chlorophenyl-SH | Ih-27 | 34.9 |
| 4-methylphenyl-SH | Ih-28 | 50.5 |
| 2-naphthyl-SH | Ih-30 | 24.3 |

Study of the Antidiabetic Activity in N0STZ Rats

The antidiabetic activity of the compounds of the formulae (I) and (II) orally was determined on an experimental model of non-insulin-dependent diabetes, induced in rats with steptozotocin.

The model of non-insulin-dependent diabetes is obtained in the rats by means of a neonatal injection (on the day of birth) of steptozotocin.

The diabetic rats used are eight weeks old. The animals are housed, from the day of birth to the day of the experiment, in an animal house at a regulated temperature of 21 to 22° C. and subjected to a fixed cycle of light (from 7 a.m. to 7 p.m.) and darkness (from 7 p.m. to 7 a.m.). Their food consisted of a maintenance diet, and water and food were given "ad libitum", with the exception of fasting two hours before the tests, during which period the food is removed (post-absorptive state).

The rats are treated orally for one (D1) or four (D4) days with the test product. Two hours after the final administration of the product and 30 minutes after anaesthetising the animals with pentobarbital sodium (Nembutal®), a 300 µL blood sample is taken from the end of the tail.

Among the compounds of the formula (I), the compounds of the family (Ih), especially the compounds of the subfamily (Ii), in particular compound Ih-1 defined previously (2-(2'-naphthylthio)-4-phenyl-4-oxobutanoic acid) and compound Ih-3 of the subfamily (Ij) (2-(4'-fluorophenylthio)-4-phenyl-4-oxobutanoic acid) were evaluated according to the experimental protocol described above.

The results presented below are expressed as a percentage change in the glycaemia on D1 and D4 (number of days of treatment) relative to D0 (before the treatment).

| Compound | D1 (20 mg) | D1 (200 mg) | D4 (20 mg) | D4 (200 mg) |
|---|---|---|---|---|
| Ih-3 | −3 | 7 | −19 | −12 |
| Ih-3 | 7 | 10 | −12 | −21 |

These results show the efficacy of the compounds, especially of the formula (Ih), in reducing glycaemia in the diabetic animals.

This antidiabetic activity is correlated with an inhibitory effect of this family of molecules on kynurenine 3-hydroxylase.

Study of the Effect on Glucose Production by the Liver
Materials and Method:

The hepatocytes are isolated from the liver of Wistar rats fasted for 24 hours, according to the method described in *Methods Cell Biol.*, 13 (1975), 29-83.

The following two methods were used:

1) The hepatocytes are cultured for 16 to 18 hours in DMEM medium in the presence of AMP cyclase/dexamethasone at respective concentrations of $5 \times 10^{-5}$ M and $5 \times 10^{-7}$ M, with preincubation of the products at the test doses. After washing in pH 7.4 PBS buffer, the cells are incubated for three hours at 37° C. in a Krebs/AMPc/DEX buffer at the above-mentioned concentrations. 0.1 µM insulin is used as reference substance. Two identical experiments are performed (Table III-1).

2) The hepatocytes are cultured for 16 to 18 hours in RPMI 1640 medium free of glucose but supplemented with 1% glutamine, 100 U/mL penicillin, 100 mg/mL streptomycin and $7 \times 10^{-5}$ M hydrocortisone hemisuccinate.

After washing in pH 7.4 PBS buffer, the cells are incubated for two hours at 37° C. in a Krebs buffer free of glucose and of insulin, containing lactate/pyruvate (10/1 mM) in the presence or absence of the test compounds. 10 µM MICA (5-methoxyindole-2-carboxylic acid) is used as reference substance. Two identical experiments are performed (Table III-2).

Quantification of the glucose is performed via a colorimetric method using glucose oxidase (IL test™ Glucose, Monarch 181633-80). The protein assay is performed on the rest of the incubation medium via the Lowry method (BIO-RAD Dc protein assay, BIO-RAD 5000116).

The results are expressed as nmoles of glucose produced per ng of proteins. The statistical test used is the t test.

Results: It was thus demonstrated that tryptophan and kynurenine are powerful inhibitors of hepatic glucose production in vitro. By way of example, compound Ih-1 (Table III 1-3) and (R)-2-benzyl-4-(4-fluorophenyl)-4-oxobutanoic acid (compound i) and (R,S)-2-benzyl-4-(3',4'-dichlorophenyl)-4-oxobutanoic acid (compound j Table IV), two kynurenine 3-hydroxylase inhibitors, were found to be powerful inhibitors of hepatic glucose production in vitro, as shown by the following results:

TABLE III-1

Products tested on primary hepatocytes
Hepatic Glucose Production
stimulated by AMPc/DEX

| Products | Test concentration | HGP % of control | Proteins % of control |
|---|---|---|---|
| Ih-1 | 1 µM | 103 | 113 |
|  | 10 µM | 83 | 117 |
|  | 100 µM | 15 | 85 |

TABLE III-2

Products tested on primary hepatocytes
Hepatic Production Glucose
Basal Lact/Pyr 2 hours

| Products | Test concentration | HGP % of control | Proteins % of control |
|---|---|---|---|
| Ih-1 | 1 µM | 10 | 94 |
|  | 10 µM | 127 | 101 |
|  | 100 µM | 95 | 96 |

TABLE IV

| Compound | Concentration (µM) | Hepatic glucose production (mmol/mg of protein) | Inhibition (%) |
|---|---|---|---|
| MICA | 10 |  | 67** |
| Compound i | 0 | 101 ± 6 | — |
|  | 1 | 88 ± 7 | 13 |
|  | 10 | 73 ± 4 | 28** |
|  | 100 | 39 ± 3 | 62** |
| Compound j | 0 | 101 ± 6 | — |
|  | 1 | 71 ± 3 | 30** |
|  | 10 | 50 ± 3 | 51** |
|  | 100 | 35 ± 1 | 65** |
| Compound k | 0 | 587 ± 12 | — |
|  | 10 | 605 ± 24 | 0 |
|  | 100 | 460 ± 12 | 22 |
| Kynurenine | 0 | 101 ± 6 | — |
|  | 1 | 99 ± 5 | 2 |
|  | 10 | 97 ± 6 | 4 |
|  | 100 | 66 ± 4 | 25** |
|  | 1000 | 22 ± 2 | 78** |
| Tryptophan | 0 | 587 ± 12 | — |
|  | 10 | 518 ± 8 | 12 |
|  | 100 | 111 ± 5 | 81** |

Study of the Effect on the Secretion of the Pancreatic Hormones Insulin and Glucagon, in N0STZ Diabetic Rats
Materials and Method:

The pancreas is taken from animals rendered diabetic by injection of streptozotocin on the day of birth (Portha et al., *Diabetes*, 23: 889-895; (1974)) and anaesthetised with pentobarbital (Nembutal: 45 mg/kg; intraperitoneal route).

The isolation and perfusion of the pancreas were performed according to a modification (Assan et al., *Nature*, 239 (1972), 125-126) of the protocol described by Sussman et al. (*Diabetes*, 15 (1966), 466-472).

The effect of the compounds or of the reference substances is tested for 35 minutes (from t=20 minutes to t=55 minutes)

in Krebs buffer in the absence of glucose, and then for 30 minutes (from t=55 minutes to t=85 minutes) in the presence of 16.5 mM glucose.

The concentration of the hormones, insulin and glucagon, secreted into the medium is measured via a competitive radio-immunoassay using the kits: Insulin-CT Cis Bio-International, Schering and Glucagon—10904—Biochem immuno system, respectively.

The results are expressed as the mean±SEM (standard error of mean) of several experiments. The statistical test used is the Scheffé test.

Results:

Effect of Tryptophan and its Metabolites on the Secretion of Insulin and Glucagon in Perfused Isolated Pancreases from N0 STZ Diabetic Rats FIG. 1 shows that tryptophan stimulates insulin secretion in a glucose-dependent manner in a diabetic rat pancreas. Similarly, FIG. 2 shows that tryptophan stimulates glucagon secretion in a glucose-dependent manner in a diabetic rat pancreas.

Kynurenic acid, like tryptophan, stimulates the secretion of insulin (FIG. 3) and of glucagon (FIG. 4) in a glucose-dependent manner in a diabetic rat pancreas.

FIG. 5 and FIG. 6 show the secretion profile for insulin and glucagon, respectively, stimulated with kynurenine (at $10^{-4}$ M and $10^{-5}$ M) in a glucose-dependent manner in a diabetic rat pancreas. This stimulation is similar to that obtained with tryptophan and kynurenic acid.

Effect of Kynurenine 3-hydroxylase Inhibitors on the Secretion of Insulin and Glucagon in Perfused Isolated Pancreases from N0 STZ diabetic rats The kynurenine 3-hydroxylase inhibitors show the same insulin and glucagon secretion profile as for tryptophan, kynurenine and kynurenic acid. This observation may be seen in FIGS. 7 and 8 (stimulation of insulin and of glucagon, respectively, with compound i) and in FIGS. 9 and 10 (stimulation of insulin and of glucagon, respectively, with compound k).

Study of the Activity on Isolated Rat Islets

Effect of the chemical compounds on insulin secretion as a function of the glucose concentration, in vitro, in isolated islets of Langerhans in static incubation:

The islets of Langerhans obtained by digestion of exocrine pancreatic tissue with collagenase, and then purified on Ficoll gradient, are incubated for 90 minutes in the presence of two concentrations of glucose, (2.8 mM or 8 mM), in the presence or absence of the chemical compound. The insulin secretion is assayed by RIA in the incubation medium.

The potential of the various chemical compounds to stimulate insulin secretion is estimated by calculating the stimulation factor*.

A compound stimulates the secretion of insulin if this factor is greater than or equal to 130% for a given dose of insulin.

*NB: stimulation factor $= \dfrac{(G + \text{Product}) * 100}{G}$ where:
G=secretion of insulin (pmol/min. islet)
  in the presence of glucose alone
G+Product=secretion of insulin (pmol/min. islet)
  in the presence of the same concentration of glucose and of the test chemical compound.

FIG. 11 shows the insulin secretion for compounds Ih-18 and (i) at $10^{-5}$ M at glucose concentrations of 2.8 mM and 8 mM.

The invention claimed is:

1. A method for treating diabetes or a complication thereof comprising administering to a patient in need thereof an effective amount of one of the following compounds
2-benzylthio-4-phenyl-4-oxobutanoic acid;
2-(4'-methylphenylthio)-4phenyl-4-oxobutanoic acid;
2-(4'-chlorophenylthio)-4phenyl-4-oxobutanoic acid;
2-(4'-fluorophenylthio)-4phenyl-4-oxobutanoic acid;
2-(4'-methoxyphenylthio)4phenyl-4-oxobutanoic acid;
2-phenylthio-4-phenyl-4-oxobutanoic acid;
2-carboxymethylthio-4-phenyl-4-oxobutanoic acid;
2-cyclohexylthio-4-phenyl-4-oxobutanoic acid;
2-(2'-naphthylthio)-4-phenyl-4-oxobutanoic acid;
ethyl 2-phenylthio-4-phenyl-4-oxobutanoate;
ethyl 2-(4'-fluorophenylithio)-4-phenyl-4-oxobutanoate;
ethyl 2-(4'-chlorophenylthio)-4-phenyl-4-oxobutanoate;
ethyl 2-(4'-methylphenylthio)-4-phenyl-4- oxobutanoate;
ethyl 2-(4'-methoxyphenylthio)-4-phenyl-4- oxobutanoate;
ethyl 2-(2'-naphthylthio)-4phenyl-4-oxobutanoate;
ethyl 2-cyclohexylthio-4-phenyl-4-oxobutanoate;
ethyl 2-benzylthio-4-phenyl-4-oxobutanoate;
2-phenylthio-4-(4'-methoxyphenyl)-4-oxobutanoic acid;
2-(4'-fluorophenylthio)-4-(4'-methoxyphenyl)-4-oxobutanoic acid;
2-(4'-chlorophenylthio)-4-(4'-methoxyphenyl)-4-oxobutanoic acid;
2-(4'-methylphenylithio)-4-(4'-methoxyphenyl)-4-oxobutanoic acid;
2-(4'-methoxyphenylthio)-4-(4'-methoxyphenyl)-4-oxobutanoic acid;
2-(2'-naphthylthio)-4-(4'-methoxyphenyl)-4-oxobutanoic acid;
2-cyclohexylthio-4-(4'-methoxyphenyl)-4-oxobutanoic acid;
2-benzylthio-4-(4'-methoxyphenyl)-4-oxobutanoic acid;
2-phenylthio-4-(4'-chlorophenyl)-4-oxobutanoic acid;
2-(4'-fluorophenylthio)-4-(4'-chlorophenyl)-4-oxobutanoic acid;
2-(4'-methylphenylthio)-4-(4'-chlorophenyl)-4-oxobutanoic acid;
2-(4'-methoxyphenylithio)-4-(4'-chlorophenyl)-4-oxobutanoic acid;
2-(2'-naphthylthio)4(4'-chlorophenyl)-4-oxobutanoic acid; or

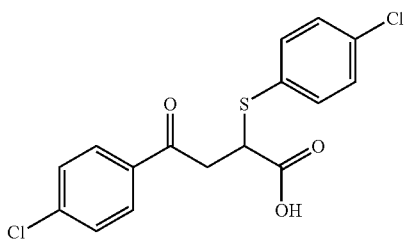

or a geometrical or optical isomer thereof,
or a tautomeric form thereof;
or a salt thereof with a pharmaceutically acceptable acid or base.

2. A method according to claim 1, wherein the risk of hypoglycaemia is reduced.

3. A method according to claim 1, wherein non-insulin-dependent diabetes or a complication thereof is treated.

4. A method according to claim 1, wherein diabetes is treated.

5. A method according to claim 1, wherein a complication of diabetes is treated.

6. A compound, which is
2-benzylthio-4-phenyl-4-oxobutanoic acid;
2-(4'-methylphenylthio)-4phenyl-4-oxobutanoic acid;
2-(4'-chlorophenylthio)-4-phenyl-4-oxobutanoic acid;
2-(4'-fluorophenylthio)-4-phenyl-4-oxobutanoic acid;
2-(4'-methoxyphenylthio)-4-phenyl-4-oxobutanoic acid;
2-phenylthio-4-phenyl-4-oxobutanoic acid;
2-carboxymethylthio-4-phenyl-4-oxobutanoic acid;
2-cyclohexylthio-4-phenyl-4-oxobutanoic acid;
2-(2'-naphthylthio)-4-phenyl-4-oxobutanoic acid;
ethyl 2-phenylithio-4-phenyl-4-oxobutanoate;
ethyl 2-(4'-fluorophenylthio)-4-phenyl-4- oxobutanoate;
ethyl 2-(4'-chlorophenylthio)-4-phenyl-4- oxobutanoate;
ethyl 2-(4'-methylphenylthio)-4-phenyl-4- oxobutanoate;
ethyl 2-(4'-methoxyphenylthio)-4-phenyl-4- oxobutanoate;
ethyl 2-(2'-naphthylthio)-4-phenyl-4-oxobutanoate;
ethyl 2-cyclohexylthio-4-phenyl-4-oxobutanoate;
ethyl 2-benzylthio-4-phenyl-4-oxobutanoate;
2-phenylthio-4-(4'-methoxyphenyl)-4-oxobutanoic acid;
2-(4'-fluorophenylthio)-4-(4'-methoxyphenyl)-4- oxobutanoic acid;
2-(4'-chlorophenylthio)-4-(4'-methoxyphenyl)-4-oxobutanoic acid;
2-(4'-methylphenylthio)-4-(4'-methoxyphenyl)-4-oxobutanoic acid;
2-(4'-methoxyphenylthio)-4-(4'-methoxyphenyl)-4-oxobutanoic acid;
2-(2'-naphthylthio)-4-(4'-methoxyphenyl)-4-oxobutanoic acid;
2-cyclohexylthio-4-(4'-methoxyphenyl)-4- oxobutanoic acid;
2-benzylthio-4-(4'-methoxyphenyl)-4-oxobutanoic acid;
2-phenylthio-4-(4'-chlorophenyl)-4-oxobutanoic acid;
2-(4-fluorophenylthio)-4-(4'-chlorophenyl)-4- oxobutanoic acid;
2-(4'-methylphenylthio)-4-(4'-chlorophenyl)-4-oxobutanoic acid;
2-(4'-methoxyphenylthio)-4-(4'-chlorophenyl)-4-oxobutanoic acid;
2-(2'-naphthylthio)-4-(4'-chlorophenyl)-4- oxobutanoic acid; or

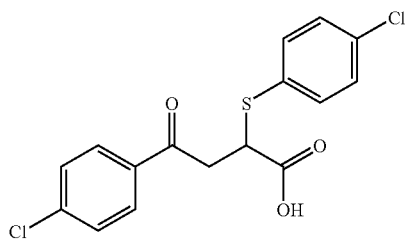

or a geometrical or optical isomer thereof,
or a tautomeric form thereof;
or a salt thereof with a pharmaceutically acceptable acid or base,
or a pharmaceutically acceptable prodrug thereof.

7. A method according to claim 1, comprising administering to a patient in need thereof an effective amount of one of the following compounds
2-benzylthio-4-phenyl-4-oxobutanoic acid;
2-(4'-methylphenylthio)-4-phenyl-4-oxobutanoic acid;
2-(4'-chlorophenylthio)-4-phenyl-4-oxobutanoic acid;
2-(4'-fluorophenylthio)-4-phenyl-4-oxobutanoic acid;
2-(4'-methoxyphenylthio)-4-phenyl-4-oxobutanoic acid;
2-phenylthio-4-phenyl-4-oxobutanoic acid;
2-carboxymethylthio-4-phenyl-4-oxobutanoic acid;
2-cyclohexylthio-4-phenyl-4-oxobutanoic acid;
2-(2'-naphthylthio)-4-phenyl-4-oxobutanoic acid;
ethyl 2-phenylthio-4-phenyl-4-oxobutanoate;
ethyl 2-(4'-fluorophenylthio)-4-phenyl-4- oxobutanoate;
ethyl 2-(4'-chlorophenylthio)-4-phenyl4- oxobutanoate;
ethyl 2-(4'-methylphenylthio)-4-phenyl-4- oxobutanoate;
ethyl 2-(4'-methoxyphenylthio)-4-phenyl-4- oxobutanoate;
ethyl 2-(2'-naphthylthio)-4phenyl-4-oxobutanoate;
ethyl 2-cyclohexylthio-4-phenyl-4-oxobutanoate;
ethyl 2-benzylthio-4-phenyl-4-oxobutanoate;
2-phenylthio-4(4'-methoxyphenyl)-4-oxobutanoic acid;
2-(4'-fluorophenylthio)-4-(4'-methoxyphenyl)- 4-oxobutanoic acid;
2-(4'-chlorophenylthio)-4-(4'-methoxyphenyl)-4-oxobutanoic acid;
2-(4'-methylphenylthio)-4-(4'-methoxyphenyl)-4-oxobutanoic acid;
2-(4'-methoxyphenylthio)-4-(4'-methoxyphenyl)-4-oxobutanoic acid;
2-(2'-naphthylthio)-4-(4'-methoxyphenyl)-4-oxobutanoic acid;
2-cyclohexylthio-4-(4'-methoxyphenyl)-4- oxobutanoic acid;
2-benzylthio-4-(4'-methoxyphenyl)-4-oxobutanoic acid;
2-phenylthio-4-(4'-chlorophenyl)-4-oxobutanoic acid;
2-(4'-fluorophenylthio)-4-(4'-chlorophenyl)-4-oxobutanoic acid;
2-(4'-methylphenylthio)-4-(4'-chlorophenyl)-4-oxobutanoic acid;
2-(4'-methoxyphenylthio)-4-(4'-chlorophenyl)-4-oxobutanoic acid;
2-(2'-naphthylthio)-4-(4'-chlorophenyl)-4-oxobutanoic acid; or

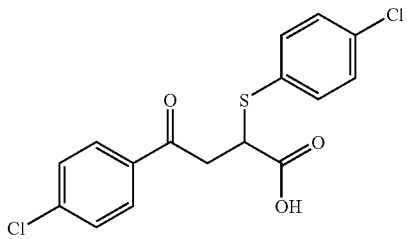

or a salt thereof with a pharmaceutically acceptable acid or base.

8. A method according to claim 6, wherein the risk of hypoglycaemia is reduced.

9. A method according to claim 6, wherein non-insulin-dependent diabetes or a complication thereof is treated.

10. A method according to claim 6, wherein diabetes is treated.

11. A method according to claim 6, wherein a complication of diabetes is treated.

12. A method according to claim 6, comprising administering to a patient in need thereof an effective amount of one of the following compounds 2-benzylthio-4phenyl-4-oxobutanoic acid;
2-(4'-methylphenylthio)-4-phenyl-4-oxobutanoic acid;
2-(4'-chlorophenylthio)-4-phenyl-4-oxobutanoic acid;
2-(4'-fluorophenylthio)-4-phenyl-4-oxobutanoic acid;
2-(4'-methoxyphenylthio)-4-phenyl-4-oxobutanoic acid;
2-phenylthio-4-phenyl-4-oxobutanoic acid;
2-(2'-naphthylthio)-4-phenyl-4-oxobutanoic acid;
ethyl 2-phenylthio-4phenyl-4-oxobutanoate;
ethyl 2-(4'-fluorophenylthio)-4-phenyl-4- oxobutanoate;
ethyl 2-(4'-chlorophenylthio)-4-phenyl-4- oxobutanoate;
ethyl 2-(4'-methylphenylthio)-4-phenyl-4- oxobutanoate;
ethyl 2-(4'-methoxyphenylthio)-4-phenyl-4- oxobutanoate;
ethyl 2-(2'-naphthylthio)4-phenyl-4-oxobutanoate;
ethyl 2-benzylthio-4-phenyl-4-oxobutanoate;
2-phenylthio-4-(4'-methoxyphenyl)-4-oxobutanoic acid;
2-(4'-fluorophenylthio)-4-(4'-methoxyphenyl)-4-oxobutanoic acid;
2-(4'-chlorophenylthio)-4(4'-methoxyphenyl)-4-oxobutanoic acid;
2-(4'-methylphenylthio)-4-(4'-methoxyphenyl)-4-oxobutanoic acid;
2-(4'-methoxyphenylthio)-4-(4'-methoxyphenyl)4oxobutanoic acid;
2-(2'-naphthylthio)-4-(4'-methoxyphenyl)-4-oxobutanoic acid;
2-benzylthio-4-(4'-methoxyphenyl)-4-oxobutanoic acid;
2-phenylthio-4-(4'-chlorophenyl)-4-oxobutanoic acid;
2-(4'-fluorophenylthio)-4-(4'-chlorophenyl)-4-oxobutanoic acid;
2-(4'-methylphenylthio)-4-(4'-chlorophenyl)-4-oxobutanoic acid;
2-(4'-methoxyphenylthio)-4-(4'-chlorophenyl)-4-oxobutanoic acid;
2-(2'-naphthylthio)-4-(4'-chlorophenyl)-4-oxobutanoic acid; or

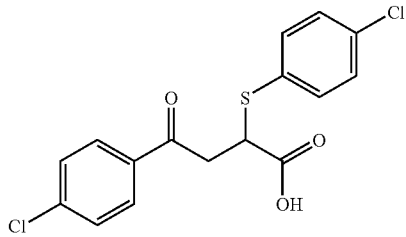

or a salt thereof with a pharmaceutically acceptable acid or base.

13. A method according to claim 6, comprising administering to a patient in need thereof an effective amount of one of the following compounds 2-carboxymethylthio-4phenyl-4-oxobutanoic acid;
or a salt thereof with a pharmaceutically acceptable acid or base.

14. A method according to claim 6, comprising administering to a patient in need thereof an effective amount of one of the following compounds 2-cyclohexylthio-4-phenyl-4-oxobutanoic acid;
ethyl 2-cyclohexylthio-4-phenyl-4-oxobutanoate; or
2-cyclohexylthio-4-(4'-methoxyphenyl)-4-oxobutanoic acid;
or a salt thereof with a pharmaceutically acceptable acid or base.

* * * * *